(12) United States Patent
Podobinski et al.

(10) Patent No.: US 8,404,799 B2
(45) Date of Patent: *Mar. 26, 2013

US008404799B2

(54) METHODS AND SYSTEMS FOR GENERATING NANOPARTICLES

(75) Inventors: John Podobinski, Boston, MA (US); J. Michael Ramstack, Lunenburg, MA (US); David S. Dickey, Dayton, OH (US)

(73) Assignee: Cerulean Pharma Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/479,646

(22) Filed: May 24, 2012

(65) Prior Publication Data

US 2012/0263653 A1 Oct. 18, 2012

Related U.S. Application Data

(63) Continuation of application No. 13/023,163, filed on Feb. 8, 2011, now Pat. No. 8,207,290.

(60) Provisional application No. 61/317,783, filed on Mar. 26, 2010.

(51) Int. Cl.
*C08G 64/00* (2006.01)
*C08G 63/02* (2006.01)
(52) U.S. Cl. .............. 528/361; 210/194; 525/450
(58) Field of Classification Search .......... 210/194; 525/450; 528/361
See application file for complete search history.

(56) References Cited

U.S. PATENT DOCUMENTS

| | | | |
|---|---|---|---|
| 3,267,074 A | 8/1966 | Wood | |
| 3,286,992 A | 11/1966 | Armeniades et al. | |
| 4,511,258 A | 4/1985 | Federighi et al. | |
| 5,049,322 A | 9/1991 | Devissaguet et al. | |
| 5,118,528 A | 6/1992 | Fessi et al. | |
| 5,650,173 A | 7/1997 | Ramstack et al. | |
| 5,654,008 A | 8/1997 | Herbert et al. | |
| 5,869,103 A | 2/1999 | Yeh et al. | |
| 5,945,126 A | 8/1999 | Thanoo et al. | |
| 6,331,317 B1 | 12/2001 | Lyons et al. | |
| 6,338,859 B1 | 1/2002 | Leroux et al. | |
| 6,395,304 B2 | 5/2002 | Lyons et al. | |
| 6,407,079 B1 | 6/2002 | Muller et al. | |
| 6,634,825 B2 | 10/2003 | Tolkoff et al. | |
| 6,638,994 B2 | 10/2003 | Crooks et al. | |
| 6,705,757 B2 | 3/2004 | Lyons et al. | |
| 6,939,033 B2 | 9/2005 | Lyons et al. | |
| 6,942,767 B1 | 9/2005 | Fazzina et al. | |
| 6,998,051 B2 | 2/2006 | Chattopadhyay et al. | |
| 7,147,806 B2 | 12/2006 | Castor | |
| 7,179,484 B2 | 2/2007 | Singh | |
| 7,270,808 B2 | 9/2007 | Cheng et al. | |
| 7,300,671 B2 | 11/2007 | Lyons et al. | |
| 7,495,052 B2 | 2/2009 | Raiche et al. | |
| 7,504,088 B2 | 3/2009 | Riley et al. | |
| 7,510,730 B2 | 3/2009 | Lyons et al. | |
| 7,550,441 B2 | 6/2009 | Farokhzad et al. | |
| 7,811,605 B2 | 10/2010 | Moro et al. | |
| 8,207,290 B2 * | 6/2012 | Podobinski et al. | 528/499 |
| 2002/0142017 A1 | 10/2002 | Simonnet | |
| 2004/0091546 A1 | 5/2004 | Johnson et al. | |
| 2007/0122440 A1 | 5/2007 | Macosko et al. | |
| 2007/0158266 A1 | 7/2007 | Shekunov et al. | |
| 2007/0282034 A1 | 12/2007 | Patel et al. | |
| 2008/0081074 A1 | 4/2008 | Gu et al. | |
| 2008/0193518 A1 | 8/2008 | Zarkadas et al. | |
| 2008/0248126 A1 | 10/2008 | Cheng et al. | |
| 2009/0169635 A1 | 7/2009 | Schwarz et al. | |
| 2009/0324552 A1 | 12/2009 | Lichter et al. | |
| 2010/0104655 A1 | 4/2010 | Zale et al. | |
| 2010/0152077 A1 | 6/2010 | Allston et al. | |
| 2010/0210465 A1 | 8/2010 | Li et al. | |
| 2011/0237748 A1 | 9/2011 | Podobinski et al. | |
| 2012/0196990 A1 * | 8/2012 | Ramstack et al. | 525/450 |

FOREIGN PATENT DOCUMENTS

| | | |
|---|---|---|
| WO | 97/41837 A2 | 11/1997 |
| WO | 02/078674 A1 | 10/2002 |
| WO | 2007/127380 A2 | 11/2007 |
| WO | 2008/070270 A2 | 6/2008 |
| WO | 2009/095448 A1 | 8/2009 |
| WO | 2010/005721 A2 | 1/2010 |
| WO | 2010/005723 A2 | 1/2010 |
| WO | 2010/005725 A2 | 1/2010 |
| WO | 2010/005726 A2 | 1/2010 |
| WO | 2010/005740 A2 | 1/2010 |
| WO | 2010/036211 A1 | 4/2010 |
| WO | 2010/114770 A1 | 10/2010 |

OTHER PUBLICATIONS

Anton et al., Design and production of nanoparticles formulated from nano-emulsion templates—a review. J Control Release. Jun. 24, 2008;128(3):185-99. Epub Feb. 23, 2008.

Aqil et al., Preparation of stable suspensions of gold nanoparticles in water by sonoelectrochemistry. Ultrason Sonochem. Sep. 2008;15(6):1055-61. Epub Apr. 22, 2008.

Aumelas et al., Nanoparticles of hydrophobically modified dextrans as potential drug carrier systems. Colloids Surf B Biointerfaces. Sep. 1, 2007;59(1):74-80. Epub May 3, 2007.

Balazs, et al., Nanoparticle Polymer Composites: Where Two Small Worlds Meet, Science (2006) 1107-1110, vol. 314.

(Continued)

*Primary Examiner* — Terressa Boykin

(74) *Attorney, Agent, or Firm* — Reza Mollaaghababa; Thomas J. Engellenner; Pepper Hamilton LLP

(57) ABSTRACT

In one aspect, the present invention provides a process for forming polymeric nanoparticles, which comprises using a static mixer to create a mixed flowing stream of an antisolvent, e.g., by introducing a liquid anti-solvent into a static mixer, and introducing a polymer solution into the mixed flowing anti-solvent stream such that controlled precipitation of polymeric nanoparticles occurs. The nanoparticles can then be separated from the anti-solvent steam.

62 Claims, 18 Drawing Sheets

OTHER PUBLICATIONS

Bilati, et al., Development of a nanoprecipitation method intended for the entrapment of hydrophilic drugs into nanparticles, European Journal of Pharmaceutical Sciences (2005) 67-75, vol. 24.

Bouchemal et al., Simultaneous emulsification and interfacial polycondensation for the preparation of colloidal suspensions of nanocapsules, Materials Science and Engineering: C (2005) 472-480, vol. 26, No. 2-3.

Bourne, et al., "Micromixing and Fast Chemical Reactions in Static Mixers", Chem. Eng. Process, vol. 30, 23-30 (1991).

Brigger et al., Nanoparticles in cancer therapy and diagnosis, Advanced Drug Delivery Reviews (2002) 631-651, vol. 54.

Cai et al., Charged nanoparticles as protein delivery systems: a feasibility study using lysozyme as model protein. Eur J Pharm Biopharm. May 2008;69(1):31-42. Epub Oct. 12, 2007.

Charcosset, Membrane processes in biotechnolgoy: An overview (2006) 482-492, vol. 24, No. 5, ISSN: 0734-9750.

Cheng et al., Stabilizer-free poly(lactide-co-glycolide) nanoparticles for multimodal biomedical probes (2008) 2104-2112, vol. 29, No. 13, ISSN: 0142-9612.

Cheng, et al., A microscal multi-inlet vortex nanoprecipitation reactor: Turbulence measurement and simulation, Applied Physics Letters, vol. 94, 204104-1 through 204104-3 (2009).

Chognot et al., Surfactive water-soluble copolymers for the preparation of controlled surface nanoparticles by double emulsion/solvent evaporation. Colloids Surf B Biointerfaces. Oct. 1, 2007;59(2):194-207. Epub May 18, 2007.

Choi et al., Thermodynamic parameters on poly ctide-co-glycolide) particle size in emulsification-diffusion process, Colloids and Surfaces A: Physicochemical and Engineering Aspects (2002) 283-289, vol. 201.

Dalwadi et al., Purification of PEGylated nanoparticles using tangential flow filtration (TFF). Drug Dev Ind Pharm. Sep. 2007;33(9):1030-9.

Dalwadi et al., Comparison and validation of drug loading parameters of PEGylated nanoparticles purified by a diafiltration centrifugal device and tangential flow filtration. Drug Dev Ind Pharm. Dec. 2008;34(12):1331-42.

Derakhshandeh et al., Encapsulation of 9-nitrocamptothecin, a novel anticancer drug, in biodegradable nanoparticles: factorial design, characterization and release kinetics. Eur J Pharm Biopharm. Apr. 2007;66(1):34-41. Epub Sep. 22, 2006.

Dong et al., Encapsulation of lipophilic drugs within enteric microparticles by a novel coacervation method. Int J Pharm. Dec. 1, 2006;326(1-2):128-38. Epub Jul. 15, 2006.

Dong et al., Methoxy poly(ethylene glycol)-poly(lactide) (MPEG-PLA) nanoparticles for controlled delivery of anticancer drugs. Biomaterials. Jun. 25, 2004;(14):2843-9.

Dong et al., Poly(D,L-lactide-co-glycolide) (PLGA) nanoparticles prepared by high pressure homogenization for paclitaxel chemotherapy. Int J Pharm. Sep. 5, 2007;342(1-2):208-14. Epub May 6, 2007.

Dong, et al., "A continuous and highly effective static mixing process for antisolvent precipitation of nanoparticles of poorly water-soluble drugs", International Journal of Pharmaceutics, vol. 386, No. 1-2 (Nov. 13, 2009), pp. 256-261.

Douroumis et al., Enhanced dissolution of Oxcarbazepine microcrystals using a static mixer process, Science Direct (2007) 208-214, vol. 59.

Douroumis et al., Using a Modified Shepards Method for Optimization of a Nanoparticulate Cyclosporine A Formulation Prepared by a Static Mixer Technique, Journal of Pharmaceutical Sciences (2008) 919-930 vol. 97 No. 2.

Fessi et al., Nanocapsule formation by interfacial polymer deposition following solvent displacement; International Journal of Pharmaceutics (1989) R1-R4, vol. 55.

Freitas et al., Solvent extraction employing a static micromixer: a simple, robust and versatile technology for the microencapsulation of proteins, Journal of Microencapsulation (2003) 67-85, vol. 20, No. 1.

Galindo-Rodriguez et al., Physicochemical Parameters Associated with Nanoparticle Formation in the Salting-out, Emulsification-Diffusion, and Nanoprecipitation Methods, Pharmaceutical Research (2004) 1428-1439, vol. 21, No. 8.

Galindo-Rodriguez, et al., Comparative scale-up of three methods for producing ibuprofen-loaded nanoparticles, European Journal of Pharmaceutical Sciences (2005) 357-367, vol. 25.

Ganachaud et al., Nanoparticles and Nanocapsule Created Using the Ouzo Effect: Spontaneous Emulsification as an Alternative to Ultrasonic and High-Shear Devices; ChemPhysChem (2005) 209-216, vol. 6.

Gindy et al., Composite Block Copolymer Stabilized Nanoparticles: Simultaneous Encapsulation of Organic Actives and Inorganic Nanostructures, Langmuir (2008) 83-90, vol. 24, American Chemical Society.

Gindy et al., Preparation of Poly(ethylene glycol) Protected Nanoparticles with Variable Bioconjugate Ligand Density, Biomacromolecules (2008) 2705-2711, vol. 9, American Chemical Society.

Govender et al., PLGA nanoparticles prepared by nanoprecipitation: drug loading and release studies of a water soluble drug, Journal of Controlled Release (1999) 171-185, vol. 57.

Hans et al., Biodegradable nanoparticles for drug delivery and targeting, Current Opinion in Solid State and Materials Science (2002) 319-327, Philadelphia, PA.

Her et al., Continuous precipitation of monodispersed colloidal particles, Journal of Materials Research (1996) 156-161.

Horn et al., Organic Nanoparticles in the Aqueous Phase—Theory, Experiment, and Use, Angew. Chem. Int. Ed. (2001) 4330-4361.

Hornig, et al., Synthetic polymeric nanoparticles by nanoprecipitation, J. Mater. Chem., (2009) 19, 3838-3840.

International Search Report and Written Opinion mailed May 24, 2011 for Application No. PCT/US2011/024062 (17 Pages).

International Search Report and Written Opinion mailed May 8, 2012 for Application No. PCT/US2012/022500 (9 Pages).

Jobmann et al., Submicronparticles from biodegradable polymers, International Journal of Pharmaceutics (2002) 213-217, vol. 242.

Johnson et al., Flash NanoPrecipitation of Organic Actives and Block Copolymers using a Confined Impinging Jets Mixer, Aust. J. Chem. (2003) 1021-1024, vol. 56.

Karnik et al., Microfluidic Platform for Controlled Synthesis of Polymeric Nanoparticles, Nano Letters, (2008) pp. 2906-2912, vol. 8, No. 9.

Legrand et al., Influence of polymer behaviour in organic solution on the production of polylactide nanoparticles by nanoprecipitation. Int J Pharm. Nov. 1, 2007;344(1-2):33-43. Epub May 31, 2007.

Lemarchand et al., Polysaccharide-decorated nanoparticles. Eur J Pharm Biopharm. Sep. 2004;58(2):327-41.

Leo et al., Nanoparticle formulation may affect the stabilization of an antiischemic prodrug. Int J Pharm. Jan. 3, 2006;307(1):103-13. Epub Nov. 14, 2005.

Letchford et al., In vitro human plasma distribution of nanoparticulate paclitaxel is dependent on the physicochemical properties of poly(ethylene glycol)-block-poly(caprolactone) nanoparticles. Eur J Pharm Biopharm. Feb. 2009;71(2):196-206. Epub Aug. 15, 2008.

Lince et al., Strategies to control the particle size distributio of poly-e- caprolactone nanoparticles for pharmaceutical applications, Science Direct (2008) 505-515, vol. 322.

Lindenberg, et al., "Experimental characterization and multi-scale modeling of mixing in static mixers," Chemical Engineering Science 63 (2008) 4135-4149.

Liu et al., Mixing in a Multi-Inlet Vortex Mixer (MIVM) for Flash NonoPrecipitation.

Liu, et al., "Mixing in a Multi-Inlet Vortex Mixer (MIVM) for Flash NanoPrecipitation," Chemical Engineering Science, vol. 63, Issue 11, pp. 2829-2842 (Jun. 2008).

Liu, et al., Formulating nanoparticles by flash nanoprecipitation for drug delivery and sustained release, Dissertation Abstracts International (2007) vol. 68 No. 9.

Lopedota et al., Research paper; The use of Eudragit RS 100/ cyclodextrin nanoparticles for the transmucosal administration of glutathione, European Jouranl of Pharmaceutics and Biopharmaceutics (2009) 509-520, vol. 72, No. 3.

Maa, et al., Effect of primary emulsions on microsphere size and protein-loading in the double emulsion process, J. Microencapsulation (1997) 225-241, vol. 14.

Mohanraj et al., Nanoparticles—A Review, Tropical Journal of Pharmaceutical Research (2006) 561-573, vol. 5.

Nagasawa et al., Design of a New Micromixer for Instant Mixing Based on the Collision of Micro Segments; Chem. Eng. Technol. (2005) vol. 28 No. 3.

Paul, et al., "Handbook of Industrial Mixing: Science and Pratice", A John Wiley & Sons, Inc., Publication (Nov. 2003).

Peukert et al., Control of aggregation in production and handling of nanoparticles, Chemical Engineering and Processing (2005) 245-252, vol. 44.

Pinon-Segundo et al., Preparation of nanoparticles by Solvent Displacement Using a Novel Recirculation System, Pharmaceutical Development and Technology (2006) 493-501.

Rivera et al., A Model for the Precipitation of Pentaerythritol Tetranitrate (PETN), Ind. Eng. Chem. Process Des. Dev. vol. 17, No. 2, 182-188 (1978).

Schwarzer et al., Combined Experimental/Numerical Study on the Precipitation of Nanoparticles, AlChE Journal (2004) 3234-3247, vol. 50, No. 12.

Silva et al., A Novel Continuous Industrial Process for Producing Hydroxyapatite Nanoparticles, Journal of Dispersion Science and Technology (2008) 542-547 vol. 29.

Soppimath, et al., Biodegradable polymeric nanoparticles as drug delivery devices, Journal of Controlled Release (2001), 1-20, vol. 70.

Streiff, et al., "The Design and Application of Static Mixer Technology" 3rd International Symposium on Mixing in Industrial Processes, Osaka, JP 1999; 107-114.

Timko et al., Magnetite polymer nanospheres loaded by Indomethacin for anti-inflammatory therapy. Journal of Magentism and Magnetic Materials. May 2006;300(1):e191-e194.

Vauthier et al., Methods for the Preparation and Manufacture of Polymeric Nanoparticles (2008), Pharmaceutical Research.

Wei et al., Historical Perspectives; Biodegradable poly([var epsilon]-caprolactone)-poly(ethylene glycol) copolymers as drug delivery stystem, International Journal of Pharmaceutics (2009) 1-18, vol. 381 No. 1.

Xie, et al.., "Fabrication of PLGA nanoparticles with a fluidic nanoprecipitation system", Journal of Nanobiotechnology (2010).

Závisové et al., Encapsulation of indomethacin in magnetic biodegradable polymer nanoparticles. Journal of Magnetism and Magnetic Materials. Apr. 2007;311(1):379-382.

* cited by examiner

METHODS AND SYSTEMS FOR GENERATING NANOPARTICLES

RELATED APPLICATION

The present application claim priority as a continuation application to U.S. patent application entitled, "Methods and systems for generating nanoparticles" filed Feb. 8, 2011 and having a Ser. No. 13/023,163, which is herein incorporated by reference in its entirety and which in turn claims priority to a provisional application entitled "Methods and systems for generating nanoparticles" filed Mar. 26, 2010 and having a Ser. No. 61/317,783, which is herein incorporated by reference in its entirety.

BACKGROUND

The present invention relates generally to methods, devices and systems for fabricating nanoparticles, and more particularly to such methods, devices and systems that can be employed to generate polymeric nanoparticles.

A variety of methods are known for generating nanoparticles. In one such method, commonly known as nanoprecipitation or flash precipitation, a polymer solution comprising a polymer dissolved in a process solvent is brought into contact with another solvent (also known as anti-solvent) in which the process solvent is miscible but the polymer is not. As a result, the process solvent diffuses rapidly into the anti-solvent while the polymer aggregates into a plurality of nanoparticles.

The conventional nanoprecipitation processes, however, suffer from a number of shortcomings. For example, it is difficult to control predictably the average particle size and the size distribution of the generated nanoparticles. Further, many challenges exist in scaling up such processes to generate nanoparticles on a large scale.

Accordingly, there is a need for enhanced methods, devices and systems for generating nanoparticles.

SUMMARY

In one aspect, the present invention provides a process for forming polymeric nanoparticles, which comprises introducing an anti-solvent into a static mixer to create a mixed flowing stream of the anti-solvent and introducing a polymer-carrying liquid, e.g., a polymer solution, or a polymer dispersion or a mixed polymer solution/dispersion, into the mixed flowing stream of the anti-solvent so as to form polymeric nanoparticles. The polymeric nanoparticles can be formed via non-reactive or reactive aggregation of at least one polymer, and in some cases one or more additives, of the polymer solution, or of the polymer dispersion or of the mixed polymer solution/dispersion, as well as in some embodiments a colloid stabilizer of the anti-solvent. For example, the polymeric nanoparticles can be formed via assembly/growth of at least one polymer, and in some cases one or more additives, of the polymer solution, or of the polymer dispersion or of the mixed polymer solution/dispersion, as well as in some embodiments a colloid stabilizer of the anti-solvent. An example of reactive aggregation can include generating the polymeric nanoparticles via formation of covalent chemical bonds. An example of non-reactive aggregation can include generating the polymeric nanoparticles via assembly without formation of covalent chemical bonds.

For example, the nanoparticles can be formed by precipitation (e.g., a controlled precipitation through selection of various parameters, such as the flow rate of the anti-solvent and/or the flow rate and/or the polymer concentration of the polymer solution (or of the polymer dispersion or of the mixed polymer solution/dispersion)). The nanoparticles can then be separated from the anti-solvent stream. Although in the following description, various aspects and embodiments of the invention are primarily described by reference to a polymer solution, the teachings of the invention can also be practiced with a polymer dispersion and/or a mixed polymer solution/dispersion.

The dimensions of the static mixer, e.g., its length and diameter, can vary over a wide range. By way of example, in some embodiments the static mixer can have a diameter greater than about 1 cm, or greater than about 2 cm, or greater than about 10 cm, or larger. For example, the static mixer can have a diameter in a range of about 1 cm to about 100 cm, or in a range of about 20 cm to about 80 cm, or in a range of about 30 cm to about 70 cm, or in a range of about 40 cm to about 60 cm. In some embodiments, the static mixer can have between about 1 to about 24 mixing elements. By way of example, the number of the mixing elements can be in a range of about 12 to about 24. In some embodiments, the number of mixing elements is in a range of about 1 to about 4. In some embodiments, the static mixer is configured to cause substantially isotropic mixing of a fluid over at least about 50%, or at least about 60%, or at least about 70%, or at least about 80%, or at least about 90%, or over the entire volume of a portion of a conduit in which the static mixer is disposed.

A variety of flow rates, flow velocities and mixing conditions can be employed. In some embodiments, the anti-solvent flowing stream is introduced into the static mixer at a flow rate in a range of about 20 ml/min to about 2000 ml/min, e.g., in a range of about 20 ml/min to about 1500 ml/min, or in a range of about 30 ml/min to about 1000 ml/min, or in a range of about 40 ml/min to about 500 ml/min, or in a range of about 20 ml/min to about 400 ml/min, or in a range of about 20 ml/min to about 300 ml/min, or in a range of about 20 ml/min to about 200 ml/min, or in a range of about 20 ml/min to about 100 ml/min. In some embodiments, the anti-solvent flowing stream exhibits an average axial flow velocity in a range of about 1 cm/sec to about 100 cm/sec (e.g., in a range of about 1.5 cm/sec to about 60 cm/sec). By way of example, in some embodiments, the anti-solvent flowing stream can exhibit an average axial flow velocity in a range of about 1 cm/sec to about 10 cm/sec, or in a range of about 10 cm/sec to about 20 cm/sec, or in a range of about 20 cm/sec to about 30 cm/sec, or in a range of about 30 cm/sec to about 40 cm/sec, or in a range of about 40 cm/sec to about 50 cm/sec, or in a range of about 50 cm/sec to about 60 cm/sec, or in a range of about 60 cm/sec to about 70 cm/sec, or in a range of about 70 cm/sec to about 80 cm/sec, or in a range of about 80 cm/sec to about 90 cm/sec, or in a range of about 90 cm/sec to about 100 cm/sec. In many embodiments, the polymer solution is introduced into the mixed flowing stream of the anti-solvent as a liquid stream.

A wide range of ratios of the flow rate of the mixed flowing stream of the anti-solvent relative to that of the polymer solution stream can be employed. For example, the ratio of the anti-solvent flow rate relative to the polymer solution flow rate can be in a range of about 1:1 to about 100:1, e.g., in a range of about 1:1 to about 10:1, or in a range of about 1:1 to about 20:1, or in a range of about 1:1 to about 30:1, or in a range of about 1:1 to about 40:1, or in a range of about 1:1 to about 50:1, or in a range of about 1:1 to about 60:1, or in a range of about 1:1 to about 70:1, or in a range of about 1:1 to about 80:1, or in a range of about 1:1 to about 90:1. In some embodiments, the flow rate of the anti-solvent stream is about 10 times greater than the flow rate of the polymer solution stream. In some embodiments, the polymer solution is introduced into the mixed flowing stream of the anti-solvent as a liquid stream at an axial flow velocity in a range of about 0.5 cm/sec to about 40 cm/sec, for example, in a range of about 2 cm/sec to about 20 cm/sec.

The nanoparticles can be formed via precipitation, typically over a short time period, upon contact of the polymer solution with the mixed flowing stream of the anti-solvent. For example, the nanoparticles can be generated via precipitation within a time period less than about 10 milliseconds (e.g., a time period in a range of about 1 millisecond to about 10 milliseconds, or in a range of about 2 milliseconds to about 10 milliseconds), or within a time period less than about 5 milliseconds (e.g., a time period in a range of about 1 millisecond to about 5 milliseconds, or a time period in a range of about 2 milliseconds to about 5 milliseconds) upon exposure of the polymer solution to the mixed flowing stream of the anti-solvent. For example, in some embodiments, at least about 50%, or at least about 60%, or at least about 70%, or at least about 80%, or at least about 90%, or all of the nanoparticles are formed within a time period less than about 10 milliseconds (e.g., a time period in a range of about 1 millisecond to about 10 milliseconds, or a time period in a range of about 2 milliseconds to about 10 milliseconds), or within a time period less than about 5 milliseconds (e.g., a time period in a range of about 1 millisecond to about 5 milliseconds, or a time period in a range of about 2 milliseconds to about 5 milliseconds) upon exposure of the polymer solution to the mixed flowing stream of the anti-solvent. In an embodiment, the time period over which the nanoparticles are generated can be adjusted by controlling, e.g., the flow rate of the anti-solvent flowing stream, the concentration of the polymer solution, the concentration of the colloid stabilizer, among others. For example, in an embodiment, as the flow rate of the anti-solvent flowing stream increases the time period over which the nanoparticles are generated decreases.

The polymer solution (and in some embodiments a polymer dispersion or a mixed polymer solution/dispersion) can be introduced into the mixed flowing stream of the anti-solvent at a variety of locations. For example, the static mixer can extend from a proximal end to a distal end and the polymer solution can be introduced into the mixed flowing stream of the anti-solvent at an intermediate location between the proximal and distal ends of the static mixer. Alternatively, the polymer solution can be introduced into the mixed flowing stream of the anti-solvent in proximity to the proximal end of said static mixer. In other embodiments, the polymer solution can be introduced into the mixed anti-solvent flowing stream in proximity to the distal end of the static mixer.

In a related aspect, the nanoparticles generated by the above process exhibit a polydispersity index equal to or less than about 0.25. By way of example, the nanoparticles can exhibit a polydispersity index in a range of about 0.05 to about 0.1.

In a related aspect, in the above process for fabricating nanoparticles, the flow rate of the mixed flowing stream of the anti-solvent can be changed so as to adjust an average particle size of the polymeric nanoparticles. By way of example, the flow rate of the anti-solvent stream can be selected such that the polymeric nanoparticles exhibit an average particle size equal to or less than about 200 nm while exhibiting in some cases a particle size distribution less than about 100 nm. Further, in some embodiments, the flow rate of the anti-solvent stream can be selected such that the polymeric nanoparticles will exhibit an average particle size equal to or less than about 100 nm, e.g., in a range of about 40 nm to about 100 nm. By way of example, in some embodiments, the flow rate of the mixed flowing stream of the anti-solvent can be varied between about 100 ml/min to about 1800 ml/min to adjust the average particle size of the polymeric nanoparticles in a range of about 100 nm to about 230 nm.

In a related aspect, the flow rate of the mixed flowing stream of the anti-solvent can be selected to be in a range in which an average particle size of the polymeric nanoparticles is substantially independent of the anti-solvent flow rate. Alternatively, the flow rate of mixed flowing stream of the anti-solvent can be selected to be in a range in which an average particle size of the polymeric nanoparticles is strongly dependent on the anti-solvent flow rate. For example, in an embodiment, when the flow rate of the mixed flowing stream of the anti-solvent is less than about 200 ml/min, e.g., in a range of about 20 ml/min to about 200 ml/min, or in a range about 20 ml/min to about 100 ml/min, the average particle size of the polymeric nanoparticles is strongly dependent on the anti-solvent flow rate. For example, in an embodiment, when the flow rate of the mixed flowing stream of the anti-solvent is greater than about 200 ml/min, e.g., greater than about 300 ml/min (e.g., in a range of about 300 ml/min to about 1000 ml/min, or in a range of about 500 ml/min to about 2000 ml/min), the average particle size of the polymeric nanoparticles is substantially independent of the anti-solvent flow rate.

In a related aspect, the average axial flow velocity of the mixed flowing stream of the anti-solvent or that of the polymer solution can be selected to be in a range in which an average particle size of the nanoparticles is substantially independent of such axial flow velocity. Alternatively, the average axial flow velocity of the mixed flowing stream of the anti-solvent or that of the polymer solution can be selected to be in a range in which an average particle size of the nanoparticles is strongly dependent on such flow velocity.

In another aspect, a ratio of a flow rate of the anti-solvent stream relative to a flow rate of the polymer solution can be changed so as to adjust an average particle size of the polymeric nanoparticles.

In some embodiments, the method for forming polymeric nanoparticles can include the additional steps of selecting one or more parameters, e.g., anti-solvent and/or polymer solution flow rate, polymer concentration in the polymer solution, the average axial flow velocity of the mixed flowing stream of the anti-solvent and/or that of the polymer solution, or other parameters discussed herein, and carrying out the method under such selected conditions. Optionally, the method can include evaluating a sample of the nanoparticles produced to determine if the nanoparticles meet one or more predefined criteria, e.g., average particle size, polydispersity, drug loading, etc. In some embodiments, if the sample of the nanoparticles fails to meet the one or more predefined criteria, one or more of the parameters, such as those listed above, can be adjusted and the method carried out under the adjusted conditions. Again, a sample of the nanoparticles produced can be evaluated to determine if the nanoparticles meet the one or more predefined criteria. This process can be repeated, if needed, until a sample of the nanoparticles that meets the one or more predefined criteria is achieved.

In some embodiments, at least one attribute of a sample of nanoparticles produced (e.g., an average particle size, polydispersity, drug loading, etc), or that of its preparation, can be compared with a reference value for that attribute. The reference value can be, e.g., a release parameter or a manufacturing specification, e.g., one set by a regulatory agency, e.g., the FDA or EMEA, a compendial authority, or a manufacturer. In an embodiment, the reference value is a value exhibited by a preparation previously made by the method. In an embodiment, e.g., responsive to whether the attribute meets a reference value for that attribute a further decision or step is taken, e.g., the sample is classified, selected, rejected, accepted, or discarded, released or withheld, processed into a drug product, shipped, moved to a different location, formulated, labeled, packaged, released into commerce, exported, imported, or sold or offered for sale, depending on whether the preselected criterion is met. For example, based on the result of the evaluation, the batch from which a sample is taken can be processed, e.g., as just described. For example, if the criterion is met, the preparation is sold, shipped, or offered for sale or otherwise released into commerce.

The polymer solution can comprise a polymer dissolved in a process solvent, wherein the process solvent is miscible, or at least partially miscible, with the anti-solvent. In some embodiments, the concentration of the polymer in the polymer solution can be changed so as to adjust an average particle size of the polymeric nanoparticles. A variety of polymers can be employed. By way of example, the polymer can be any of poly(lactide-co-glycolide), poly(lactide), poly(epsilon-caprolactone), poly(isobutylcyanoacrylate), poly(isohexylcyanoacrylate), poly(n-butylcyanoacrylate), poly(acrylate), poly(methacrylate), poly(lactide)-poly(ethylene glycol), poly(lactide-co-glycolide)-poly(ethylene glycol), poly(epsilon-caprolactone)-poly(ethylene glycol), and poly(hexadecylcyanoacrylate-co-poly(ethylene glycol)cyanoacrylate).

In some embodiments, the polymer solution can include at least one additive. The additive can be any of a therapeutic agent or an imaging agent. In some embodiments, such a therapeutic or imaging agent can be coupled to, associated with, or incorporated in the polymer. For example, in some embodiments, such a therapeutic or imaging agent can be conjugated to, or embedded in the polymer. In some embodiments, multiple different agents can be coupled to, associated with, or incorporated in the polymer. In some embodiments, the imaging agent can be coupled to the therapeutic agent By way of example, the therapeutic agent can be, without limitation, any of an anti-neoplastic agent, an anti-inflammatory agent, a cardiovascular active agent, or an anti-metabolite.

In some embodiments, the therapeutic agent can be any of a taxane, an epothilone, a boronic acid proteasome inhibitor, and an antibiotic.

In some embodiments, the imaging agent can be, without limitation, any of a radioactive or non-radioactive agent, or a fluorescent agent. Some examples of suitable imaging agents include, without limitation, Technetium Bicisate, Ioxaglate, Fluorodeoxyglucose, label-free Raman imaging agents, encapsulate MRI contrast agent Gd-DTPA, and rhodamine 6G as a fluorescent agent. In some embodiments, the imaging agent can be radiolabeled docetaxel (e.g., 3H-radiolabeled docetaxel or 14C-radiolabeled docetaxel), or radiolabeled paclitaxel.

The process solvent can include, without limitation, any of acetone, ether, alcohol, tetrahydrofuran, 2-pyrrolidone, N-Methyl-2-pyrrolidone (NMP), dimethylformamide (DMF), dimethylacetamide (DMA), methyl acetate, ethyl formate, methyl ethyl ketone (MEK), methyl isobutyl ketone (MIBK), methyl propyl ketone, isopropyl ketone, isopropyl acetate, acetonitrile (MeCN) and dimethyl sulfoxide (DMSO).

In some embodiments, the anti-solvent can include an aqueous solution. By way of example, the aqueous solution can include any of an alcohol or an ether, and water. In some embodiments, the anti-solvent can include an organic solvent or a mixture of two or more organic solvents. For example, the anti-solvent can include, without limitation, any of methanol, ethanol, n-propanol, isopropanol, n-butanol, and ethyl ether.

In some embodiments, the anti-solvent can include a colloid stabilizer. By way of example, the colloid stabilizer can include, without limitation, any of poly(vinyl alcohol), Dextran and pluronic F68, poly(vinyl pyrrolidone), solutol, Tween 80, poloxamer, carbopol, poly-ethylene glycol, sodium dodecyl sulfate, poly($\epsilon$-caprolactone), peptides, and carbohydrates.

In some embodiments, the polymer solution is delivered as a liquid stream that intersects the anti-solvent stream at a non-zero angle. The angle can be an acute angle, for example, one in a range of about 10 degrees to about 90 degrees (e.g., in a range of about 50 degrees to about 90 degrees). In some embodiments, the angle can be in a range of about 10 degrees to about 170 degrees. In some other embodiments, the polymer solution is injected into the flowing stream of the anti-solvent.

In another aspect, the step of separating the nanoparticles includes collecting the nanoparticles downstream from the static mixer as a suspension in a mixture of the anti-solvent and a process solvent of the polymer solution. At least a portion of the process solvent can be removed from the suspension in order to concentrate the suspension. For example, the suspension can be diafiltered to remove at least a portion of the process solvent.

In some embodiments, a lyoprotectant can be added to the preparation, e.g., the suspension. It can be added prior to or after the step of concentrating the suspension, to protect the nanoparticles in a subsequent lyophilization step. By way of example, the lyoprotectant can be, without limitation, a derivatized cyclic oligosaccharide, e.g., a derivatized cyclodextrin, e.g., 2 hydroxy propyl-$\beta$cyclodextrin, e.g., partially etherified cyclodextrins (e.g., partially etherified $\beta$ cyclodextrins) disclosed in U.S. Pat. No. 6,407,079, the contents of which are incorporated herein by this reference.

In another aspect, a process for forming polymeric nanoparticles is disclosed, which includes introducing an anti-solvent into a static mixer so as to generate a mixed flowing stream of the anti-solvent, and introducing a polymer solution (or a polymer dispersion or a mixed polymer solution/dispersion) into the mixed flowing stream of the anti-solvent to generate polymeric nanoparticles (e.g., via precipitation) such that the polymeric nanoparticles exhibit a polydispersity index equal to or less than about 0.25. For example, the polymeric nanoparticles can exhibit a polydispersity index in a range of about 0.05 to about 0.1.

In some embodiments, the polymeric nanoparticles can exhibit an average particle size equal to or less than about 500 nm. For example, the polymeric nanoparticles can exhibit an average particle size in a range of about 5 nm to about 500 nm, or in a range of about 10 nm to about 500 nm, or in a range of about 20 nm to about 500 nm, or in a range of about 30 nm to about 500 nm, or in a range of about 40 nm to about 500 nm, or in a range of about 50 nm to about 500 nm.

In some embodiments, the polymeric nanoparticles can exhibit an average particle size equal to or less than about 400 nm. For example, the polymeric nanoparticles can exhibit an average particle size in a range of about 5 nm to about 400 nm, or in a range of about 10 nm to about 400 nm, or in a range of about 20 nm to about 400 nm, or in a range of about 30 nm to about 400 nm, or in a range of about 40 nm to about 400 nm, in a range of about 50 nm to about 400 nm.

In some embodiments, the polymeric nanoparticles can exhibit an average particle size equal to or less than about 300 nm. For example, the polymeric nanoparticles can exhibit an average particle size in range of about 5 nm to about 300 nm, or in a range of about 10 nm to about 300 nm, or in a range of about 20 nm to about 300 nm, or in a range of about 30 nm to about 300 nm, or in a range of about 40 nm to about 300 nm, or in a range of about 50 nm to about 300 nm.

In some embodiments, the polymeric nanoparticles can exhibit an average particle size equal to or less than about 200 nm. For example, the polymeric nanoparticles can exhibit an average particle size in a range of about 5 nm to about 200 nm, or in a range of about 10 nm to about 200 nm, or in a range of 20 nm to about 200 nm, or in a range of about 30 nm to about 200 nm, or in a range of about 40 nm to about 200 nm, or in a range of about 50 nm to about 200 nm.

In some embodiments, the polymeric nanoparticles can exhibit an average particle size equal to or less than about 100 nm. For example, the polymeric nanoparticles can exhibit an average particle size in a range of about of 5 nm to about 100 nm, or in a range of about 10 nm to about 100 nm, or in a range of about 20 nm to about 100 nm, or in a range of about 30 nm to about 100 nm, or in a range of about 40 nm to about 100 nm, or in a range of about 50 nm to about 100 nm.

In some embodiments, the anti-solvent flow comprises a stream exhibiting a flow rate in a range of about 20 ml/min to about 2000 ml/min. In some embodiments, the mixed flowing stream of anti-solvent exhibits an average axial velocity in a range of about 1 cm/sec to about 100 cm/sec, e.g., in a range of about 1.5 cm/sec to about 60 cm/sec.

In the above process for forming polymeric nanoparticles, the polymer solution can be introduced into the mixed flowing stream of the anti-solvent at a variety of locations relative to the static mixer. For example, the polymer solution can be introduced into the mixed flowing stream of the anti-solvent at an intermediate location between a proximal end and a distal end of the static mixer. Alternatively, the polymer solution can be introduced into the mixed flowing stream of the anti-solvent in proximity to the proximal end, or the distal end, of the static mixer.

In the above process, the polymer solution can be introduced as a liquid stream into the mixed flowing stream of the anti-solvent at a variety of flow rates. For example, a flow rate of the anti-solvent stream relative to a flow rate of said polymer solution stream can be in a range of about 1:1 to about 100:1, e.g., in a range of about 1:1 to about 10:1, or in a range of about 1:1 to about 20:1, or in a range of about 1:1 to about 30:1, or in a range of about 1:1 to about 40:1, or in a range of about 1:1 to about 50:1, or in a range of about 1:1 to about 60:1, or in a range of about 1:1 to about 70:1, or in a range of about 1:1 to about 80:1, or in a range of about 1:1 to about 90:1. Further, in some embodiments, the polymer solution stream is introduced into the mixed flowing stream of the anti-solvent at a non-zero angle, e.g., an acute angle, relative to a flow direction of the anti-solvent stream. In some embodiments, the polymer solution is injected into the mixed anti-solvent stream.

The polymer solution can include a polymer dissolved in a process solvent, where the process solvent is miscible, or is at least partially miscible, with the anti-solvent. In some embodiments, the polymer solution can include at least one additive, such as a therapeutic agent or an imaging agent. A variety of therapeutic agents and imaging agents can be employed, such as those listed above. In some embodiments, one or more of such agents are coupled to, associated with, or incorporated in the polymer. In some embodiments, multiple different agents can be coupled to, associated with, or incorporated in the polymer. In some embodiments, one or more of such agents are conjugated to, or embedded in the polymer.

A variety of polymers, process solvents and anti-solvents can be employed in the above process. Some examples of such polymers, process solvents and anti-solvents are provided above. In some embodiments, the anti-solvent can include a colloid stabilizer, such as those listed above.

In another aspect, the invention provides a process for controlling particle size of nanoparticles formed, e.g., by precipitation, which comprises introducing an anti-solvent liquid flow into a static mixer to generate a mixed flowing stream of the anti-solvent, and introducing a polymer solution into the mixed flowing stream of the anti-solvent so as to generate a plurality of polymeric nanoparticles, e.g., by precipitation. The flow rate of the anti-solvent stream through said static mixer is controlled so as to adjust an average particle size of the nanoparticles.

The step of controlling the flow rate of the anti-solvent stream can include changing the flow rate so as to vary the average particle size in a range of about 50 nm to about 200 nm.

In the above process for controlling particle size of nanoparticles, the polymer solution can comprise a polymer dissolved in a process solvent that is miscible, or at least partially miscible, in the anti-solvent. In some embodiments, the polymer solution can include an additive, such as a therapeutic or an imaging agent. In some embodiments, one or more of such agents are embedded in the polymer. In some embodiments, one or more of such agents are conjugated to the polymer. Some examples of suitable therapeutic and imaging agents are provided above.

A variety of polymers, process solvents and anti-solvents can be employed in the above process. Some examples of such polymers, process solvents and anti-solvents are provided above.

In some embodiments, the anti-solvent can include a colloid stabilizer. Some examples of suitable colloid stabilizers are provided above.

In another aspect, a system for generating polymeric nanoparticles is disclosed, which comprises a conduit having a first input port for receiving an anti-solvent, and at least one static mixer disposed in the conduit to generate a mixed flowing stream of the anti-solvent, where the static mixer extends from a proximal end to a distal end. The conduit has a second input port disposed relative to the static mixer so as to allow introducing a polymer solution into the mixed flowing stream of the anti-solvent to generate polymeric nanoparticles, e.g., via precipitation. The system can further include a device, e.g., a variable pump, adapted to cause a flow of the anti-solvent from a reservoir to the conduit and to control a flow rate of the anti-solvent through the static mixer for adjusting an average particle size of the nanoparticles.

In some embodiments, the conduit in which the static mixer is disposed has an internal diameter of at least about 1 mm, or at least about 10 mm, or at least about 100 mm, or at least 500 mm.

In some embodiments, the device for causing the anti-solvent flow is adapted to control a flow rate of said anti-solvent through the conduit within a range of about 20 ml/min to about 2000 ml/min.

In some embodiments, the second input port is located at an intermediate location between the proximal and distal ends of the static mixer. In some other embodiments, the second input port is located in proximity to the proximal end, or the distal end, of the static mixer. In some embodiments, the second input port is configured so as to allow introduction of the polymer solution into the conduit at a non-zero angle, e.g., at an acute angle (e.g., wherein the angle between the direction of flow through the conduit and the direction of flow entering the conduit through the second input port is in a range of about 50 degrees to about 90 degrees), relative to a flow direction of the anti-solvent stream.

In some embodiments, the system includes at least one injector coupled to the second input port for injecting the polymer solution into the mixed flowing stream of the anti-solvent.

In some embodiments, the system can further include a reservoir for containing a quantity of the polymer solution. A device adapted to cause a flow of the polymer solution, e.g., a pump, can cause the polymer solution to flow from the reservoir through the second input port into the conduit. The device can be capable of adjusting the flow rate of the polymer solution through the second port. For example, the device can be adapted to control the flow rate of the polymer solution through the second input port in a range of about 4 ml/min to about 200 ml/min, for example, in a range of about 5 ml/min to about 100 ml/min.

In the above system, the conduit can comprise an output port through which the polymeric nanoparticles exit the conduit as a suspension in a mixture of the anti-solvent and a process solvent of the polymer solution. A collection vessel coupled to the output port of the conduit can collect the suspension containing the nanoparticles. The collection vessel can contain a liquid. In many embodiments, a stirrer is disposed in the collection vessel for mixing the liquid.

In another aspect, a device for generating nanoparticles is disclosed, which comprises a conduit having a first input port for receiving a stream of an anti-solvent and an output port. A static mixer is disposed in the conduit to cause mixing of the anti-solvent stream to generate a mixed flowing stream of the anti-solvent, where the static mixer extends from a proximal end to a distal end. The conduit has a second input port positioned relative to the static mixer so as to allow delivery of a polymer solution into said mixed flowing stream of the anti-solvent for generating polymeric nanoparticles, e.g., by precipitation.

In some embodiments, the second input port is positioned at an intermediate location relative to the proximal and distal ends of the static mixer. In some alternative embodiments, the second input port is positioned in proximity to the proximal end, or the distal end, of the static mixer. In some embodiments, the second input port is positioned downstream from the static mixer and sufficiently close to the mixer to allow the delivery of the polymer solution into the mixed flowing stream of the anti-solvent.

In some embodiments, the second input port is configured so as to introduce the polymer solution into the anti-solvent stream at a non-zero angle, e.g., at an acute angle, relative to a flow direction of the mixed flowing stream of the anti-solvent. In some embodiments, the angle can be in a range of about 50 degrees to about 90 degrees.

In some embodiments, the device can further include a collection tank in fluid communication with the output port for receiving a suspension containing the polymeric nanoparticles. In some embodiments, the tank can store a quantity of an aqueous solution.

In a related aspect, the above device contains the anti-solvent and/or the polymer solution discussed above.

In another aspect, a device for generating nanoparticles is disclosed, which comprises a conduit having a first input port for receiving a stream of a liquid anti-solvent and an output port. A static mixer is disposed in the conduit to cause mixing of the anti-solvent stream to generate a mixed flowing stream of the anti-solvent, where the static mixer extends from a proximal end to a distal end. The device further includes an injector coupled to the conduit for injecting a polymer solution into the mixed flowing stream of the anti-solvent.

In some embodiments, the injector is positioned so as to inject the polymer solution at an intermediate location between the proximal and distal ends of the static mixer. Alternatively, the injector can be positioned to inject the polymer solution in proximity to the proximal, or the distal, end of the static mixer. In some embodiments, the injector is configured to inject the polymer solution into the mixed flowing stream of the anti-solvent along a direction substantially parallel to the flow direction of the anti-solvent.

In a related aspect, the device contains the anti-solvent and/or the polymer solution discussed above.

In another aspect, a process for forming polymeric nanoparticles is disclosed, which comprises using a static mixer to create a mixed flowing stream of an anti-solvent, and introducing a polymer solution into the mixed flowing stream of the anti-solvent such that controlled precipitation of polymeric nanoparticles occurs. In some embodiments, a flow rate of the mixed flowing stream of the anti-solvent and/or that of the polymer solution can be controlled so as to adjust an average particle size of the nanoparticles.

In another aspect, a process for monitoring nanoparticles formed by introducing a polymer solution into a mixed flowing stream of an anti-solvent is disclosed, which includes selecting one or more parameters, such as, the flow rate of the anti-solvent stream, the polymer solution flow rate, the concentration of polymer in the polymer solution, and the concentration of a colloid stabilizer in the anti-solvent. The polymer solution is introduced, under such conditions, into a mixed flowing stream of the anti-solvent, which is created by introducing the anti-solvent into a static mixer, so as to form polymeric nanoparticles, e.g., by precipitation. The nanoparticles produced are then examined to determine if one or more of their attributes (e.g., their average particle size or polydispersity index) meet one or more predefined criteria. If they do not, one or more of the above parameters are adjusted, and polymer solution is introduced, under the adjusted conditions, into the mixed flowing stream of the anti-solvent to generate a new population of nanoparticles. The new population of the nanoparticles can be examined to determine if one or more of their attributes meet the predefined criteria. The above steps are repeated until a population of nanoparticles whose one or more attributes meet the predefined criteria is achieved.

In another aspect, a plurality of polymeric nanoparticles are generated by using the above processes.

In another aspect, a population of polymeric nanoparticles having an average particle size in a selected range, e.g., one of the ranges described above, is generated by using the above processes.

In another aspect, a population of polymeric nanoparticles having a polydispersity index less than about 0.25, e.g., in a range of about 0.05 to about 0.1, is generated by using the above processes.

In a related aspect, a population of polymeric nanoparticles that includes at least about 10 grams, or at least about 20 grams, or at least about 30 grams, or at least about 40 grams, or at least about 50 grams, or at least about 100 grams, or at least about 200 grams, or at least about 300 grams, or at least about 400 grams, or at least about 500 grams, or at least about 1000 grams of the nanoparticles is generated by using the above processes.

In a related aspect, a population of polymeric nanoparticles having poly(lactic-co-glycolic acid) (PLGA) as at least one polymeric component is generated by using the above processes. In some embodiments, the PLGA polymer is attached to a therapeutic agent. For example, the therapeutic agent can be an anti-neoplastic agent. In some embodiments, the anti-neoplastic agent is a taxane (e.g., paclitaxel, docetaxel, larotaxel, or cabazitaxel).

In another aspect, a pharmaceutically acceptable preparation of polymeric nanoparticles is generated by using the above processes. In an embodiment, the pharmaceutically acceptable preparation includes, e.g., a pharmaceutically acceptable excipient, e.g., a lyoprotectant. In an embodiment, the pharmaceutically acceptable preparation is a liquid or a lyophilized powder.

In an embodiment, a process described herein further includes dividing a first pharmaceutically acceptable preparation made by a process described herein into smaller aliquots and optionally packaging a plurality of aliquots into gas and/or liquid tight containers.

In an embodiment, a process described herein further includes testing the product (e.g., the preparation of the nanoparticles) to determine if it meets a preselected reference value, e.g., a value for concentration, average particle size, purity, polydispersity index, or other particle properties described herein.

Further understanding of the invention can be obtained by reference to the following detailed description in conjunction with the associated drawings, which are described briefly below.

DETAILED DESCRIPTION

Figure 1:
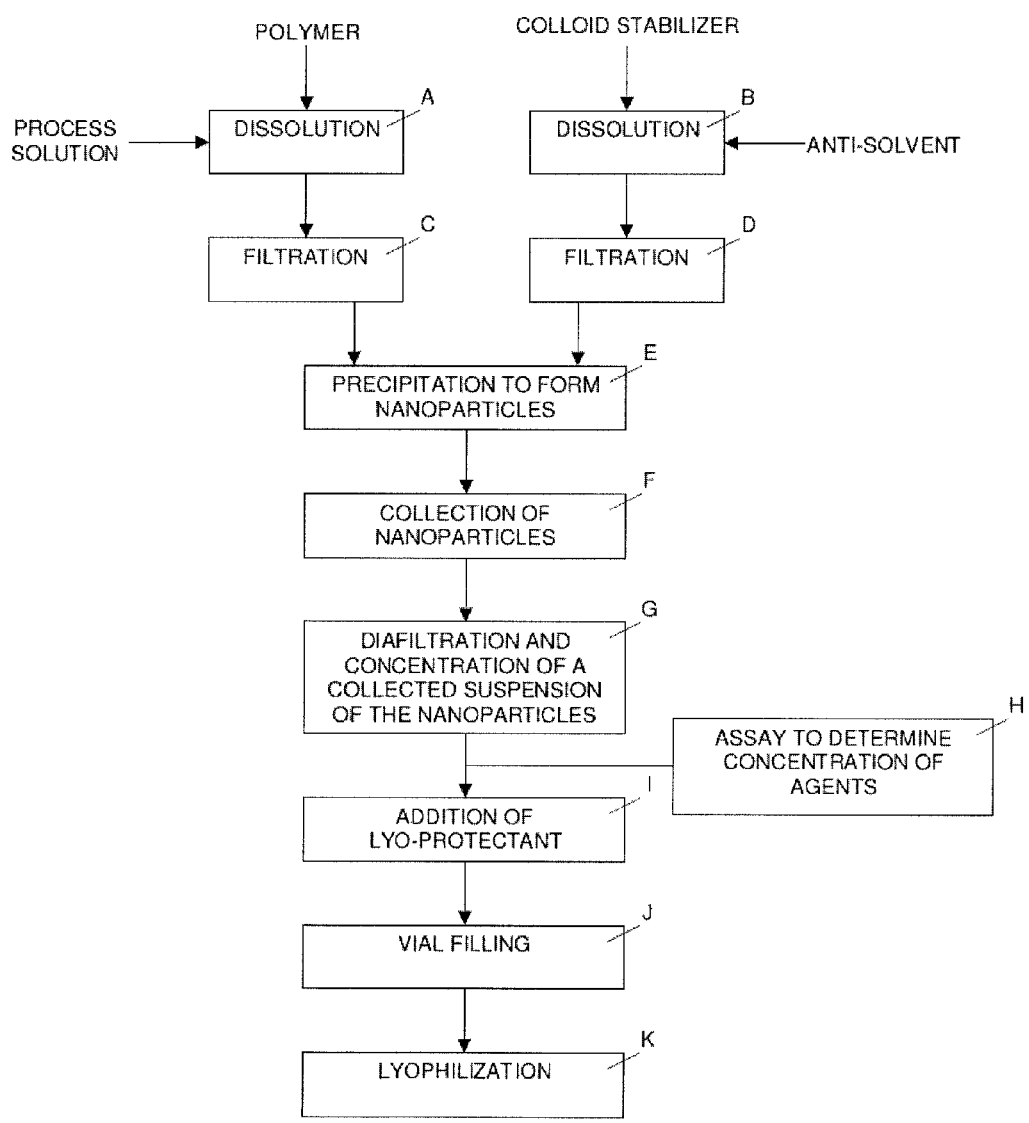
FIG. 1 is a flow chart depicting various steps in an exemplary embodiment of a method according to the invention for generating polymeric nanoparticles.

The present invention relates generally to methods, devices and systems for generating nanoparticles, e.g., polymeric nanoparticles. In some embodiments, the nanoparticles are formed by introducing a polymer solution, which comprises one or more polymer(s) dissolved in a process solvent, into a mixed flowing stream of an anti-solvent, which is miscible, or at least partially miscible, with the process solvent but in which the polymer(s) cannot be dissolved in any appreciable amount, to cause precipitation of the polymer(s) into a plurality of nanoparticles. As discussed in more detail below, it has been discovered that utilizing a static mixer to generate a mixed flowing stream of the anti-solvent, and introducing the polymer solution into such a mixed flowing stream to cause precipitation can provide significant advantages. For example, it allows forming the nanoparticles with a low polydispersity index over a wide range of anti-solvent (and polymer solution) flow rates. It has also been discovered that the anti-solvent flow rate and/or the polymer solution flow rate can be changed to adjust the average particle size of the fabricated nanoparticles. The low polydispersity index exhibited by the nanoparticles can be beneficial in a variety of applications such as pharmaceutical applications. Moreover, the precipitation process can be scaled up to form nanoparticles on a large scale.

The following definitions are provided for a variety of terms and phrases utilized herein:

Static Mixer:

The term "static mixer" or "motionless mixer" as used herein refers to a device that includes one or more substantially stationary mixing elements, e.g., baffles such as blades, plates, vanes, that are adapted for placement in the path of a flowing fluid, e.g., a fluid flowing through a conduit, to produce a pattern of flow divisions and splits to accomplish mixing, e.g., radial mixing via radial circulation or exchange, in the flowing fluid. Although the stationary mixing elements are typically immovable within the conduit, some limited movement of the stationary elements relative to the conduit can occur so long as such limited movement does not contribute substantially to the mixing of the flowing fluid. In a static mixer having multiple stationary elements, these elements are typically arranged in series and in a staggered orientation relative to one another.

Mixed Flowing Stream:

The term "mixed flowing stream" as used herein refers to a flowing stream of a fluid, e.g., a liquid, that exhibits active motion normal to its direction of flow.

Polymer Solution:

The term "polymer solution" as used herein refers to a solution comprising one or more polymers dissolved in a liquid solvent, which is herein also referred to as process solvent. The polymer(s) are typically sufficiently soluble in the solvent such that a concentration of at least about 0.1 percent by weight, and preferably at least about 0.2 percent by weight, of the polymer(s) can be dissolved in the solvent at room temperature. In some cases, the concentration of the polymer(s) that can be dissolved in the solvent at room temperature can be optionally less than about 10 percent by weight, e.g., less than about 5 percent by weight. The polymer solution can also include a variety of additives, such as therapeutic and/or imaging agents or other supplemental additives useful for the production and/or subsequent use of the nanoparticles.

Anti-Solvent:

The term "anti-solvent" as used herein refers to a liquid, or a mixture of liquids, which is incapable of dissolving any appreciable concentration (e.g., a concentration equal to or greater than about 0.1% at room temperature) of the polymer(s) of the polymer solution, but is miscible, or at least partially miscible, with the process solvent. In some embodiments, the anti-solvent and the process solvent can be mixed in all proportions to form a homogeneous solution. When combined with the polymer solution, the anti-solvent causes at least a portion of the polymer to precipitate.

Average Axial Flow Velocity:

The phrase "average axial flow velocity" as used herein refers to a velocity of a fluid, e.g., liquid, along the direction of flow averaged over a cross-sectional area of the flow, e.g., averaged over a cross-sectional area of a conduit through which the fluid flows. The average axial flow velocity ($V_{ave}$) can be obtained by the following relation:

$$V_{ave} = \frac{Q}{A} \quad \text{Eq. (1)}$$

wherein,

Q represent the volumetric rate of fluid flow along the direction of flow (e.g., in units of ml/sec), and A represents a cross-sectional area of the flow, e.g., a cross-sectional area of a conduit through which the fluid flows.

Nanoparticle:

The term "nanoparticle" is used herein to refer to a material structure whose size in any dimension (e.g., x, y, and z Cartesian dimensions) is less than about 1 micrometer (micron), e.g., less than about 500 nm or less than about 200 nm or less than about 100 nm, and greater than about 5 nm. A nanoparticle can have a variety of geometrical shapes, e.g., spherical, ellipsoidal, etc. The term "nanoparticles" is used as the plural of the term "nanoparticle."

Average Particle Size:

The term "average particle size" is a length dimension which is designated herein as Z average or $Z_{ave}$, and as used herein refers to the intensity weighted mean hydrodynamic size of an ensemble collection of particles measured by dynamic light scattering (DLS). The Z average is derived from a Cumulants analysis of a measured autocorrelation curve, wherein a single particle size is assumed and a single exponential fit is applied to the autocorrelation function. The autocorrelation function ($G(\tau)$) is defined as follows:

$$G(\tau) = \langle I(t) \cdot I(t+\tau) \rangle = A[1+B \exp(-\Gamma \tau)] \quad \text{Eq. (3)}$$

wherein, $$\Gamma = Dq^2 \quad \text{Eq. (4)}$$

$$q = \frac{4\pi \tilde{n}}{\lambda_0} \sin\left(\frac{\theta}{2}\right) \quad \text{Eq. (5)}$$

$$D = \frac{kT}{6\pi\mu R_H}, \quad \text{Eq. (6)}$$

wherein,

I represents the light scattering intensity, t represents an initial time,

τ represents the delay time,

A represents an amplitude (or intercept) of the autocorrelation function,

B represents the baseline,

D represents the diffusion coefficient, q represents the scattering vector, k represents the Boltzmann constant, $\lambda_0$ represents the vacuum wavelength of a laser source employed for the light scattering measurements, ñ represents the index of refraction of the medium, θ represents the scattering angle, T represents the absolute temperature (Kelvin), μ represents the viscosity of the medium, and $R_H$ represents the hydrodynamic radius.

In the Cumulants analysis, the exponential fitting expression of Eq. (3) is expanded as indicated below as expression y(τ) in Eq. (7) to account for polydispersity, which is defined in more detail below, or peak broadening, $$y(\tau) = \frac{1}{2}\ln[G(\tau) - A] = \quad \text{Eq. (7)}$$
$$\frac{1}{2}\ln[AB\exp(-2\Gamma\tau + \mu_2\tau^2)] \cong \frac{1}{2}\ln[AB] - \langle\Gamma\rangle\tau + \frac{\mu_2}{2}\tau^2 =$$
$$a_0 - a_1\tau + a_2\tau^2$$

wherein $\mu_2$ is a fitting parameter and the other parameters are defined above.

The dynamic light scattering data can be fit to the above expression (Eq. (7)) to obtain values of the parameters $a_0$, $a_1$, and $a_2$. The first Cumulant moment ($a_1$) can be utilized to obtain $Z_{ave}$ as follows:

$$Z_{ave} = \frac{1}{a_1} \frac{kT}{3\pi\mu} \left[\frac{4\pi\tilde{n}}{\lambda_0} \sin\left(\frac{\theta}{2}\right)\right]^2 \qquad \text{Eq. (8)}$$

wherein the parameters are defined above.

The first Cumulant moment ($a_1$) and the second Cumulant moment ($a_2$) can be used to calculate another parameter known as polydispersity index (PdI), which is discussed in more detail below, as follows:

$$PdI = \frac{2a_2}{a_1^2} \qquad \text{Eq. (9)}$$

Polydispersity Index:

The term "polydispersity index" is used herein as a measure of the size distribution of an ensemble of particles, e.g., nanoparticles. The polydispersity index is calculated as indicated in the above Eq. (9) based on dynamic light scattering measurements.

Particle Size Distribution:

If it is assumed that an ensemble of particles exhibit a Gaussian size distribution, then the particle size distribution of such an ensemble is a length dimension that can be defined as the square root of the standard deviation of the Gaussian distribution ($\sigma^2$) as follows:

$$\sigma^2 = PdI \cdot Z_{ave}^2 \qquad \text{Eq. (10)}$$

$$\text{Particle Size Distribution} = \sqrt{\sigma^2} \qquad \text{Eq. (11)}$$

wherein $Z_{ave}$ is defined by Eq. (8) above.

Colloid Stabilizer:

The term colloid stabilizer as used herein refers to an additive added to the anti-solvent and/or the polymer solution to prevent or retard an unwanted alteration of the physical state of the particles, e.g., a colloid stabilizer can inhibit aggregation of the nanoparticles. For example, a colloid stabilizer can inhibit aggregation of the nanoparticles during and/or after their formation.

Lyoprotectant:

The term "lyoprotectant," as used herein refers to a substance present in a lyophilized preparation. Typically it is present prior to the lyophilization process and persists in the resulting lyophilized preparation. It can be used to protect nanoparticles, liposomes, and/or micelles during lyophilization, for example to reduce or prevent aggregation, particle collapse and/or other types of damage. In an embodiment the lyoprotectant is a cryoprotectant.

In an embodiment the lyoprotectant is a carbohydrate. The term "carbohydrate," as used herein refers to and encompasses monosaccharides, disaccharides, oligosaccharides and polysaccharides.

In an embodiment, the lyoprotectant is a monosaccharide. The term "monosaccharide," as used herein refers to a single carbohydrate unit (e.g., a simple sugar) that can not be hydrolyzed to simpler carbohydrate units. Exemplary monosaccharide lyoprotectants include glucose, fructose, galactose, xylose, ribose and the like.

In an embodiment, the lyoprotectant is a disaccharide. The term "disaccharide," as used herein refers to a compound or a chemical moiety formed by 2 monosaccharide units that are bonded together through a glycosidic linkage, for example through 1-4 linkages or 1-6 linkages. A disaccharide may be hydrolyzed into two monosaccharides. Exemplary disaccharide lyoprotectants include sucrose, trehalose, lactose, maltose and the like.

In an embodiment, the lyoprotectant is an oligosaccharide. The term "oligosaccharide," as used herein refers to a compound or a chemical moiety formed by 3 to about 15, preferably 3 to about 10 monosaccharide units that are bonded together through glycosidic linkages, for example through 1-4 linkages or 1-6 linkages, to form a linear, branched or cyclic structure. Exemplary oligosaccharide lyoprotectants include cyclodextrins, raffinose, melezitose, maltotriose, stachyose acarbose, and the like. An oligosaccharide can be oxidized or reduced.

In an embodiment, the lyoprotectant is a cyclic oligosaccharide. The term "cyclic oligosaccharide," as used herein refers to a compound or a chemical moiety formed by 3 to about 15, preferably 6, 7, 8, 9, or 10 monosaccharide units that are bonded together through glycosidic linkages, for example through 1-4 linkages or 1-6 linkages, to form a cyclic structure. Exemplary cyclic oligosaccharide lyoprotectants include cyclic oligosaccharides that are discrete compounds, such as α cyclodextrin, β cyclodextrin, or γ cyclodextrin.

Other exemplary cyclic oligosaccharide lyoprotectants include compounds which include a cyclodextrin moiety in a larger molecular structure, such as a polymer that contains a cyclic oligosaccharide moiety. A cyclic oligosaccharide can be oxidized or reduced, for example, oxidized to dicarbonyl forms. The term "cyclodextrin moiety," as used herein refers to cyclodextrin (e.g., an α, β, or γ cyclodextrin) radical that is incorporated into, or a part of, a larger molecular structure, such as a polymer. A cyclodextrin moiety can be bonded to one or more other moieties directly, or through an optional linker. A cyclodextrin moiety can be oxidized or reduced, for example, oxidized to dicarbonyl forms.

Carbohydrate lyoprotectants, e.g., cyclic oligosaccharide lyoprotectants, can be derivatized carbohydrates. For example, in an embodiment, the lyoprotectant is a derivatized cyclic oligosaccharide, e.g., a derivatized cyclodextrin, e.g., 2 hydroxy propyl-βcyclodextrin, e.g., partially etherified cyclodextrins (e.g., partially etherified β cyclodextrins) disclosed in U.S. Pat. No. 6,407,079, the contents of which are incorporated herein by this reference.

An exemplary lyoprotectant is a polysaccharide. The term "polysaccharide," as used herein refers to a compound or a chemical moiety formed by at least 16 monosaccharide units that are bonded together through glycosidic linkages, for example through 1-4 linkages or 1-6 linkages, to form a linear, branched or cyclic structure, and includes polymers that comprise polysaccharides as part of their backbone structure. In backbones, the polysaccharide can be linear or cyclic. Exemplary polysaccharide lyoprotectants include glycogen, amylase, cellulose, dextran, maltodextrin and the like.

Derivatized Carbohydrate:

The term "derivatized carbohydrate," refers to an entity which differs from the subject non-derivatized carbohydrate by at least one atom. For example, instead of the —OH present on a non-derivatized carbohydrate the derivatized carbohydrate can have —OX, wherein X is other than H. Derivatives may be obtained through chemical functionalization and/or substitution or through de novo synthesis—the term "derivative" implies no process-based limitation.

Injector:

The term "injector" as used herein refers to a device that can force, e.g., propel, a fluid, e.g., a liquid, into a receiving medium.

In some of the following embodiments, various methods for generating nanoparticles are described with reference to steps of these methods. The order in which the steps of the methods are discussed is not intended to necessarily indicate the order in which those steps must be performed.

Figure 2:
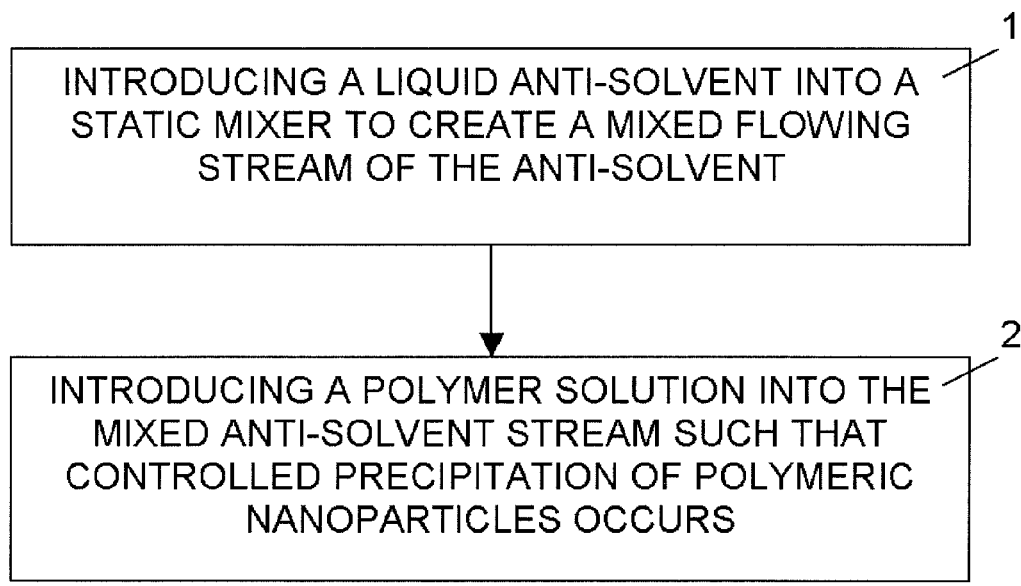
FIG. 2 is a flow chart depicting various steps according to an exemplary embodiment of the invention for performing a precipitation process for generating polymeric nanoparticles.

With reference to the flow charts of FIGS. 1 and 2, in an exemplary embodiment of a method according to the teachings of the invention for forming polymeric nanoparticles, a polymer solution can be generated by dissolving one or more polymers, such as a polymer to which a therapeutic or an imaging agent is coupled, or with which a therapeutic or an imaging agent is associated or in which a therapeutic or an imaging agent is incorporated (e.g., embedded), in a process solvent (step A). Further, an anti-solvent can be prepared (step B). While the process solvent is miscible, or at least partially miscible, with the anti-solvent, the polymer is not soluble in the anti-solvent in any appreciable amount, thereby allowing a subsequent formation of polymeric nanoparticles via a precipitation process (step E). For example, the solubility of the polymer in the anti-solvent at room temperature can be less than about 0.1% by weight. Further, any additive agent(s) added to the polymer solution is preferably not soluble in the anti-solvent in any appreciable amount. In some embodiments, the polymer solution and the anti-solvent are filter sterilized (steps C and D) prior to their use in the precipitation process.

Referring to the flow chart of FIG. 2, in an exemplary embodiment for performing the precipitation process to generate a plurality of nanoparticles (step E in the flow chart of FIG. 1), an anti-solvent is introduced into a static mixer, e.g., a static mixer disposed in a conduit, to create a mixed flowing stream of the anti-solvent (step 1). The polymer solution is introduced into the mixed flowing stream of the anti-solvent such that precipitation of the polymer into a plurality of polymeric nanoparticles occurs (step 2). The generated nanoparticles are then separated from the anti-solvent stream, e.g., in a manner discussed in more detail below.

Without being limited to any particular theory, upon contact of the polymer solution with the anti-solvent stream, precipitation of the polymer into a plurality of polymeric nanoparticles occurs as a result of rapid desolvation of the polymer. In particular, the process solvent diffuses rapidly into the anti-solvent due to its miscibility with the anti-solvent. The polymer is, however, not miscible in the anti-solvent and hence aggregates (e.g., precipitates) into a plurality of nanoparticles as the process solvent diffuses into the anti-solvent. The static mixer design, the choice of the anti-solvent and the process solvent, and in particular the mixing of the anti-solvent and the process solvent, can facilitate the mass transfer of solvents, thereby controlling the size of the nanoparticles formed via precipitation. The nanoparticles can be formed rapidly, e.g., over a milliseconds time scale. For example, in some cases the nanoparticles can form in less than about 10 milliseconds (e.g., in a range of about 1 millisecond to about 10 milliseconds), or less than about 5 milliseconds (e.g., in a range of about 1 millisecond to about 5 milliseconds), subsequent to the contact of the polymer solution with the mixed flowing stream of the anti-solvent. The rapid formation of the nanoparticles can be due to interfacial turbulence at the interface of the solvent and the anti-solvent, which can result, e.g., from flow, diffusion and surface tension variations.

As discussed in more detail below, the introduction of the polymer solution into a mixed flowing stream of the anti-solvent results in formation of polymeric nanoparticles with predictable average particle sizes and a low polydispersity index (PdI) over a wide range of anti-solvent, and polymer solution, flow rates and average axial flow velocities.

In some embodiments, the average particle size ($Z_{ave}$) can be equal to or less than about 500 nm. For example, the polymeric nanoparticles can exhibit an average particle size in a range of about 5 nm to about 500 nm, or in a range of about 10 nm to about 500 nm, or in a range of about 20 nm to about 500 nm, or in a range of about 30 nm to about 500 nm, or in a range of about 40 nm to about 500 nm, or in a range of about 50 nm to about 500 nm. In some embodiments, the average particle size ($Z_{ave}$) can be equal to or less than about 400 nm. For example, the polymeric nanoparticles can exhibit an average particle size in a range of about 5 nm to about 400 nm, or in a range of about 10 nm to about 400 nm, or in a range of about 20 nm to about 400 nm, or in a range of about 30 nm to about 400 nm, or in a range of about 50 nm to about 400 nm. In some embodiments, the average particle size ($Z_{ave}$) can be equal to or less than about 300 nm. For example, the polymeric nanoparticles can exhibit an average particle size in range of about 5 nm to about 300 nm, or in a range of about 10 nm to about 300 nm, or in a range of about 20 nm to about 300 nm, or in a range of about 40 nm to about 300 nm, or in a range of about 50 nm to about 300 nm.

In some embodiments, the average particle size ($Z_{ave}$) of the nanoparticles can be equal to or less than about 200 nm (e.g., equal to or less than about 195 nm (and, e.g., equal to or greater than about 20 nm), equal to or less than about 190 nm (and, e.g., equal to or greater than about 20 nm), equal to or less than about 185 nm (and, e.g., equal to or greater than about 20 nm), equal to or less than about 180 nm (and, e.g., equal to or greater than about 20 nm), equal to or less than about 175 nm (and, e.g., equal to or greater than about 20 nm), equal to or less than about 170 nm (and, e.g., equal to or greater than about 20 nm), equal to or less than about 165 nm (and, e.g., equal to or greater than about 20 nm), equal to or less than about 160 nm (and, e.g., equal to or greater than about 20 nm), equal to or less than about 155 nm (and, e.g., equal to or greater than about 20 nm), equal to or less than about 150 nm (and, e.g., equal to or greater than about 20 nm), equal to or less than about 145 nm (and, e.g., equal to or greater than about 20 nm), equal to or less than about 140 nm (and, e.g., equal to or greater than about 20 nm), equal to or less than about 135 nm (and, e.g., equal to or greater than about 20 nm), equal to or less than about 130 nm (and, e.g., equal to or greater than about 20 nm), equal to or less than about 125 nm (and, e.g., equal to or greater than about 20 nm), equal to or less than about 120 nm (and, e.g., equal to or greater than about 20 nm), equal to or less than about 115 nm (and, e.g., equal to or greater than about 20 nm), equal to or less than about 110 nm (and, e.g., equal to or greater than about 20 nm), equal to or less than about 105 nm (and, e.g., equal to or greater than about 20 nm), equal to or less than about 100 nm (and, e.g., equal to or greater than about 20 nm), equal to or less than about 95 nm (and, e.g., equal to or greater than about 20 nm), equal to or less than about 90 nm (and, e.g., equal to or greater than about 20 nm), equal to or less than about 85 nm (and, e.g., equal to or greater than about 20 nm), equal to or less than about 80 nm (and, e.g., equal to or greater than about 20 nm), equal to or less than about 75 nm (and, e.g., equal to or greater than about 20 nm), equal to or less than about 70 nm (and, e.g., equal to or greater than about 20 nm), equal to or less than about 65 nm (and, e.g., equal to or greater than about 20 nm), equal to or less than about 60 nm (and, e.g., equal to or greater than about 20 nm), equal to or less than about 55 nm or 50 nm (and, e.g., equal to or greater than about 20 nm)). For example, the average particle size can be in a range of about 50 nm to about 200 nm, or in a range of about 100 nm to about 200 nm.

In general, a wide range of anti-solvent and polymer solution flow rates can be employed. By way of example, the flow rate of the anti-solvent stream can be in a range of about 20 ml/min to about 2000 ml/min, and the flow rate of the polymer solution can be in a range of about 4 ml/min to about 200 ml/min, for example, in a range of about 5 ml/min to about 100 ml/min. In some embodiments, the flow rate of the anti-solvent stream is substantially greater than the flow rate of the polymer solution into the anti-solvent stream. For example, the flow rate of the anti-solvent stream can be at least about 2 times, or at least about 3 times, at least about 5 times, or at least about 10 times, greater than the flow rate of the polymer solution. In some other embodiments, the anti-solvent flow rate and the polymer solution flow rate can have a 1:1 ratio.

In some embodiments, the concentration of the polymer solution and/or the concentration of the anti-solvent can be changed so as to adjust the average particle size of the nanoparticles.

In many embodiments, the static mixer generates a mixed flowing stream of the anti-solvent that presents a substantially isotropic mixed anti-solvent environment to the incoming polymer solution, thus ensuring that the formed nanoparticles will exhibit a low polydispersity index. For example, the static mixer can create sufficient radial and/or tangential motion of the anti-solvent to rapidly create a substantially uniform mixed environment, thus facilitating formation of nanoparticles with a low polydispersity index. For example, as indicated above, the polydispersity index can be equal to or less than about 0.25, e.g., in a range of about 0.05 to about 0.1. By way of example, in some embodiments, the static mixer generates a mixed anti-solvent environment that is substantially isotropic over at least about 50%, or at least about 60%, or at least about 70%, or at least about 90%, or 100% of the volume of the conduit in which the static mixer is disposed.

Further, a mixed flowing stream of the anti-solvent can allow the introduction of the polymer solution at a variety of velocities (and corresponding momentum values) into the anti-solvent stream. Even at a low momentum, the polymer solution will encounter a highly mixed anti-solvent environment, which will lead to formation of nanoparticles with predictable average particle size and polydispersity index.

In some embodiments, the polymer solution can be introduced into the mixed flowing stream of the anti-solvent at an intermediate location of the static mixer. Alternatively, the polymer solution can be introduced into the anti-solvent flowing stream in proximity to a proximal or a distal end of the mixer. In some embodiments, the polymer solution is introduced into the mixed flowing stream of the anti-solvent at a non-zero angle, e.g., an acute angle, relative to the anti-solvent flow direction. For example, the polymer solution stream can intersect the anti-solvent flowing stream at an angle in a range of about 50 degrees to about 90 degrees. In some embodiments, the polymer solution is injected into the mixed flowing stream of the anti-solvent either at an angle relative to the direction of the anti-solvent flow or substantially parallel to the direction of the anti-solvent flow.

In some embodiments, rather that utilizing a single static mixer unit, multiple static mixer units can be employed to provide a mixed flowing stream of an anti-solvent within a selected portion of a conduit. In some such embodiments, the static mixer units are oriented in a staggered configuration relative to one another so as to enhance the mixing of the anti-solvent.

A variety of polymers, process solvents, and anti-solvents can be employed in the precipitation process to form nanoparticles. By way of example, the polymers can include the following monomers (or sub-units): acrylates, acrylonitriles such as methacrylnitrile, vinyls, aminoalkyls, styrenes, and lactic acids. Some examples of acrylates include, without limitation, methyl acrylate, ethyl acrylate, propyl acrylate, n-butyl acrylate, isobutyl acrylate, 2-ethyl acrylate, and t-butyl acrylate. Some examples of vinyls include, without limitation, vinyl acetate, vinylversatate, vinylpropionate, vinylformamide, vinylacetamide, vinylpyridines and vinylimidazole. Some examples of aminoalkyls include, without limitation, aminoalkylacrylates, aminoalkylmethacrylates and aminoalkyl(meth)acrylamides.

In some embodiments, the polymer can be an amphiphilic copolymer that is formed of monomers exhibiting different hydrophilic and hydrophobic properties. For example, in some embodiments, the polymer has a hydrophilic portion and a hydrophobic portion. In some embodiments, the polymer is a block copolymer. In some embodiments, the amphiphilic copolymer is formed of blocks (groups) of monomers or sub-units, where some blocks are substantially hydrophobic while other blocks are substantially hydrophilic. For example, in diblock copolymers the blocks are arranged as a series of two blocks having similar hydrophobic or hydrophilic properties while in triblock copolymers, the blocks are arranged as a series of three blocks having similar hydrophobic or hydrophilic properties. In some embodiments, the amphiphilic polymer comprises two regions, one of which is hydrophilic and the other hydrophobic, where the two regions together comprise at least about 70% by weight of the polymer (e.g., at least about 80%, at least about 90%, at least about 95%).

In some embodiments, the hydrophobic portion of the polymer is a biodegradable polymer (e.g., PLA, PGA, PLGA, PCL, PDO, polyanhydrides, polyorthoesters, or chitosan). In some embodiments, the hydrophobic portion of the polymer is PLA. In some embodiments, the hydrophobic portion of the polymer is PGA. In some embodiments, the hydrophobic portion of the polymer is a copolymer of lactic and glycolic acid (e.g., PLGA).

In some embodiments, the hydrophilic portion of the polymer is polyethylene glycol (PEG). In some embodiments, the hydrophilic portion of the polymer has a molecular weight of from about 1 kDa to about 20 kDa (e.g., from about 1 kDa to about 15 kDa, from about 2 kDa to about 12 kDa, from about 6 kDa to about 20 kDa, from about 5 kDa to about 10 kDa, from about 7 kDa to about 10 kDa, from about 5 kDa to about 7 kDa, from about 6 kDa to about 8 kDa, about 6 kDa, about 7 kDa, about 8 kDa, or about 9 kDa). In some embodiments, the ratio of molecular weight of the hydrophilic to hydrophobic portions of the polymer is from about 1:20 to about 1:1 (e.g., about 1:10 to about 1:1, about 1:2 to about 1:1, or about 1:6 to about 1:3).

In some embodiments, the hydrophilic portion of the polymer terminates in a hydroxyl moiety prior to conjugation to an agent. In some embodiments, the hydrophilic portion of the polymer terminates in an alkoxy moiety. In some embodiments, the hydrophilic portion of the polymer is a methoxy PEG (e.g., a terminal methoxy PEG).

In some embodiments, the hydrophilic portion of the polymer is attached to the hydrophobic portion through a covalent bond. In some embodiments, the hydrophilic portion is attached to the hydrophobic polymer through an amide, ester, ether, amino, carbamate, or carbonate bond (e.g., an ester or an amide).

In some embodiments, the polymer is a biodegradable polymer (e.g., polylactic acid (PLA), polyglycolic acid (PGA), poly(lactic-co-glycolic acid) (PLGA), polycaprolactone (PCL), polydioxanone (PDO), polyanhydrides, polyorthoesters, or chitosan). In some embodiments, the polymer is a hydrophobic polymer. In some embodiments, the polymer is PLA. In some embodiments, the polymer is PGA.

In some embodiments, the polymer is a copolymer of lactic and glycolic acid (poly(lactic-co-glycolic acid) (PLGA)). In some embodiments, the polymer is a PLGA-ester. In some embodiments, the polymer is a PLGA-lauryl ester. In some embodiments, the polymer comprises a terminal free acid prior to conjugation to an agent. In some embodiments, the polymer comprises a terminal acyl group (e.g., an acetyl group). In some embodiments, the ratio of lactic acid monomers to glycolic acid monomers is from about 0.1:99.9 to about 99.9:0.1. In some embodiments, the ratio of lactic acid monomers to glycolic acid monomers is from about 75:25 to about 25:75 (e.g., about 50:50 or about 75:25).

In some embodiments, the average molecular weight of the polymer is from about 1 kDa to about 20 kDa (e.g., from about 1 kDa to about 15 kDa, from about 2 kDa to about 12 kDa, from about 6 kDa to about 20 kDa, from about 5 kDa to about 10 kDa, from about 7 kDa to about 10 kDa, from about 5 kDa to about 7 kDa, from about 6 kDa to about 8 kDa, about 6 kDa, about 7 kDa, about 8 kDa, or about 9 kDa). In some embodiments, the polymer has a glass transition temperature of about 20° C. to about 60° C. In some embodiments, the polymer has a polymer polydispersity index equal to or less than about 2.5 (e.g., less than or equal to about 2.2, or less than or equal to about 2.0).

By way of further illustration, some examples of suitable polymers include poly(lactide-co-glycolide), poly(lactide), poly(epsilon-caprolactone), poly(isobutylcyanoacrylate), poly(isohexylcyanoacrylate), poly(n-butylcyanoacrylate), poly(acrylate), poly(methacrylate), poly(lactide)-poly(ethylene glycol), poly(lactide-co-glycolide)-poly(ethylene glycol), poly(epsilon-caprolactone)-poly(ethylene glycol), and poly(hexadecylcyanoacrylate-co-poly(ethylene glycol)cyanoacrylate).

In some embodiments, the polymer can include one or more grafted moieties, e.g., alkyl chains of 4 to 18 carbons, such as a grafted butyl group. In some embodiments, such grafted moieties can enhance the salvation of the polymer in the process solvent and/or the stability of the polymeric nanoparticles formed in the subsequent steps.

In some embodiments, a single agent is attached to a single polymer, e.g., to a terminal end of the polymer. In some embodiments, a plurality of agents are attached to a single polymer (e.g., 2, 3, 4, 5, 6, or more). In some embodiments, the agents are the same agent. In some embodiments, the agents are different agents. In some embodiments, the agent is a therapeutic agent or an imaging agent.

In an embodiment, the agent is poorly soluble in water, e.g., it has a solubility of less than about 1 mg/liter, or about 0.9 mg/liter, or about 0.8 mg/liter, or about 0.7 mg/liter, or about 0.6 mg/liter, or about 0.5 mg/liter in unbuffered water (pH of 7)_. In an embodiment, the agent has a molecular weight of between about 200 to 1500, 400 to 1500, 200 to 1000, 400 to 1000, 200 to 800, or 400 to 800 Daltons.

In some embodiments, the therapeutic agent is an anti-neoplastic agent. In some embodiments, the anti-neoplastic agent is an alkylating agent, a vascular disrupting agent, a microtubule targeting agent, a mitotic inhibitor, a topoisomerase inhibitor, an anti-angiogenic agent or an anti-metabolite. In some embodiments, the anti-neoplastic agent is a taxane (e.g., paclitaxel, docetaxel, larotaxel or cabazitaxel). In some embodiments, the anti-neoplastic agent is an anthracycline (e.g., doxorubicin). In some embodiments, the anti-neoplastic agent is an epothilone (e.g., ixabepilone, epothilone B, epothilone D, BMS310705, dehydelone or ZK-epothilone). In some embodiments, the anti-neoplastic agent is a platinum-based agent (e.g., cisplatin). In some embodiments, the anti-neoplastic agent is a pyrimidine analog (e.g., gemcitabine, premetrexed, floxuridine, fluorouracil (5-FU)).

In some embodiments, the anti-neoplastic agent is paclitaxel, attached to the polymer through the 2' or 7 carbon position, or both the 2' and 7 carbon positions. In some embodiments, the agent is linked to the polymer through the 7 position and has an acyl group at the 2' position (e.g., wherein the agent is a taxane such as paclitaxel, docetaxel, larotaxel or cabazitaxel).

In some embodiments, the anti-neoplastic agent is docetaxel. In some embodiments, the anti-neoplastic agent is docetaxel-succinate. In some embodiments, the anti-neoplastic agent is doxorubicin. In some embodiments, the anti-neoplastic agent is larotaxel. In some embodiments, the anti-neoplastic agent is cabazitaxel.

In some embodiments, the therapeutic agent is an agent for the treatment or prevention of cardiovascular disease. In some embodiments, the therapeutic agent is an agent for the treatment or prevention of an inflammatory or autoimmune disease.

In some embodiments, the agent is attached directly to the polymer, e.g., through a covalent bond. In some embodiments, the agent is attached to a terminal end of the polymer via an amide, ester, ether, amino, carbamate or carbonate bond. In some embodiments, the agent is attached to a terminal end of the polymer. In some embodiments, the polymer comprises one or more side chains and the agent is directly attached to the polymer through one or more of the side chains.

In some embodiments, a single agent is attached to a polymer. In some embodiments, multiple agents are attached to a polymer (e.g., 2, 3, 4 or more agents). In some embodiments, the agents are the same agent. In some embodiments, the agents are different agents.

In some embodiments, the agent is doxorubicin, and is covalently attached to the polymer through, e.g., an amide bond.

In some embodiments, the polymer-agent conjugate is:

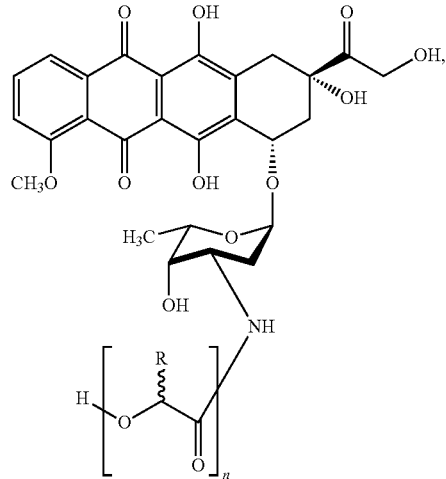

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the agent is paclitaxel, and is covalently attached to the polymer through, e.g., an ester bond.

In some embodiments, the polymer-agent conjugate is:

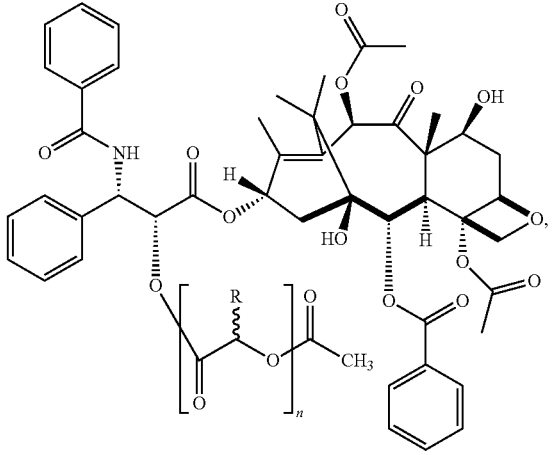

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the polymer-agent conjugate is:

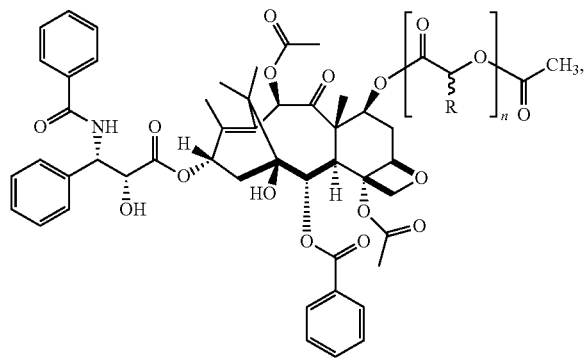

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the paclitaxel is attached through both the 2' and the 7 carbons. In some embodiments, the polymer-agent is provided as a mixture containing one or more or all of, drug-polymer species coupled through the 2' carbon, drug-polymer species coupled through the 7 carbon, and drug-polymer species coupled through both the 2' and the 7 carbons.

In some embodiments, the agent is paclitaxel, and is covalently attached to the polymer via a carbonate bond.

In some embodiments, the agent is docetaxel, and is covalently attached to the polymer through, e.g., an ester bond.

In some embodiments, the polymer-agent conjugate is:

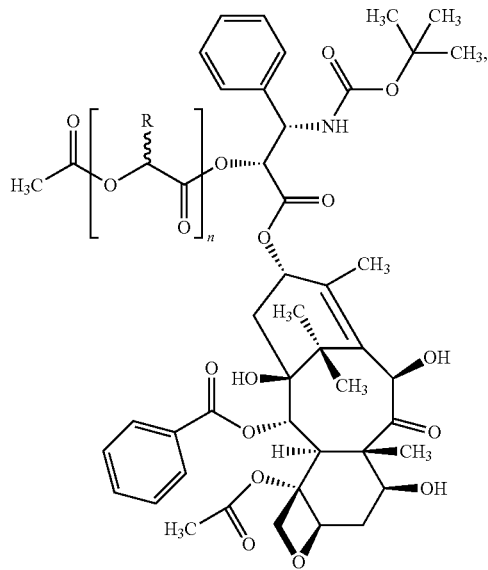

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the polymer-agent conjugate is:

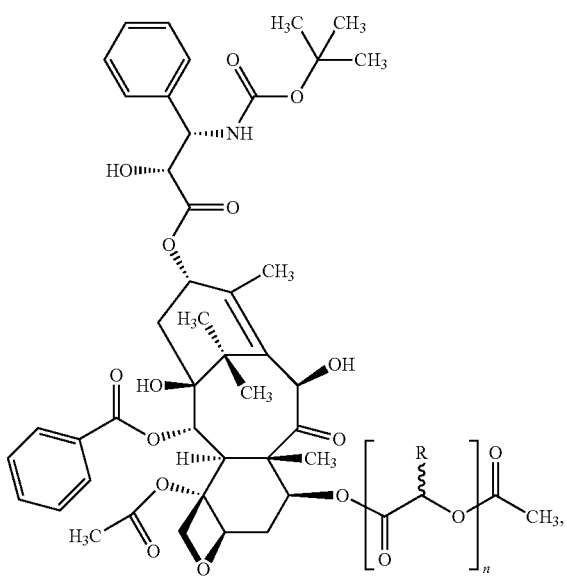

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the docetaxel is attached through both the 2' and the 7 carbons. In some embodiments, the polymer-agent is provided as a mixture containing one or more or all of, drug-polymer species coupled through the 2' carbon, drug-polymer species coupled through the 7 carbon, and drug-polymer species coupled through both the 2' and the 7 carbons.

In some embodiments, the agent is docetaxel, and is covalently attached to the polymer through a carbonate bond.

In some embodiments, the agent is attached to the polymer through a linker. In some embodiments, the linker is an alkanoate linker. In some embodiments, the linker is a PEG-based linker. In some embodiments, the linker comprises a disulfide bond. In some embodiments, the linker is a self-immolative linker. In some embodiments, the linker is an amino acid or a peptide (e.g., glutamic acid, branched glutamic acid or polyglutamic acid).

In some embodiments the linker is a multifunctional linker. In some embodiments, the multifunctional linker has 2, 3, 4 or more reactive moieties that may be functionalized with an agent. In some embodiments, all reactive moieties are functionalized with an agent. In some embodiments, not all of the reactive moieties are functionalized with an agent (e.g., the multifunctional linker has four reactive moieties, and only one, two or three react with an agent.)

In some embodiments, the polymer-agent conjugate is:

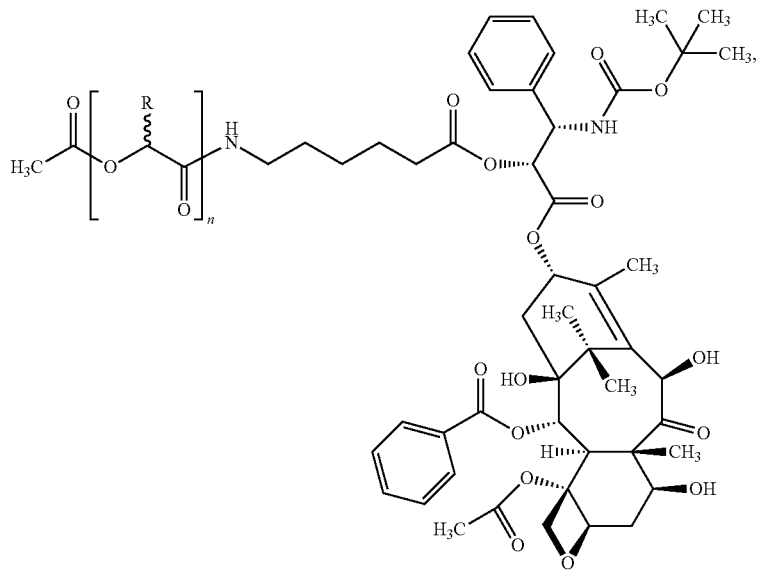

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, two agents are attached to a polymer via a multifunctional linker. In some embodiments, the two agents are the same agent. In some embodiments, the two agents are different agents. In some embodiments, the agent is docetaxel, and is covalently attached to the polymer via a glutamate linker.

In some embodiments, the polymer-agent conjugate is:

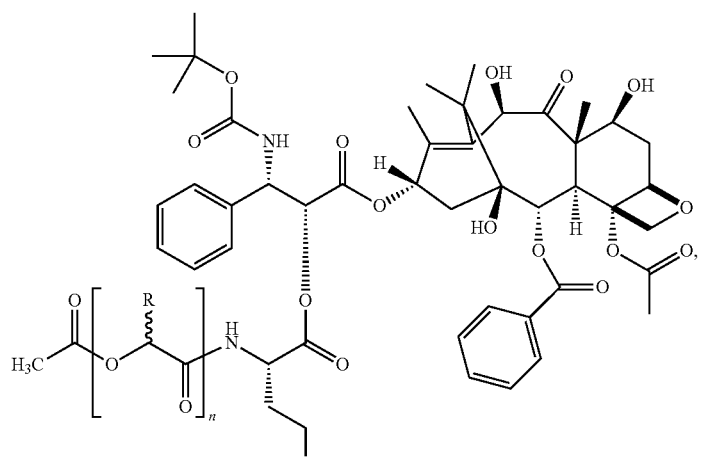

-continued

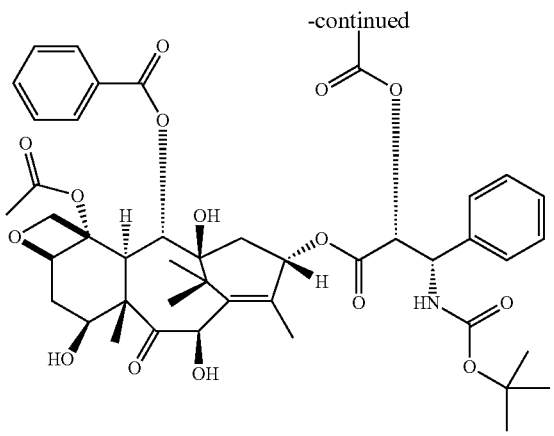

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, four agents are attached to a polymer via a multifunctional linker. In some embodiments, the four agents are the same agent. In some embodiments, the four agents are different agents. In some embodiments, the agent is docetaxel, and is covalently attached to the polymer via a bis(glutamate) linker.

In some embodiments, the polymer-agent conjugate is:

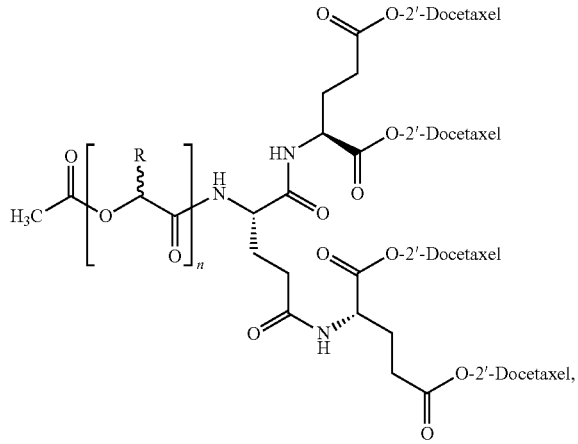

wherein 2'-docetaxel is:

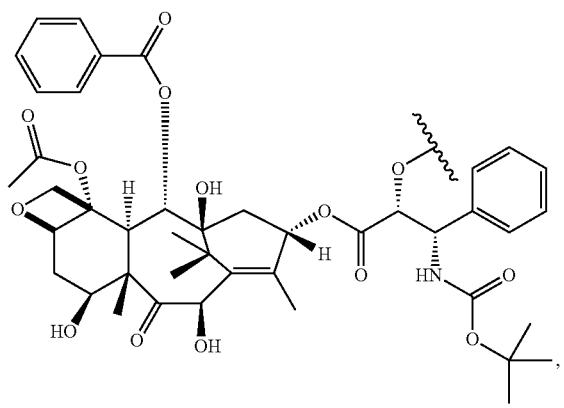

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the polymer, e.g., the hydrophilic portion of an amphiphilic copolymer, comprises a terminal conjugate. In some embodiments, the terminal conjugate is a targeting agent or a dye. In some embodiments, the terminal conjugate is a folate or a rhodamine. In some embodiments, the terminal conjugate is a targeting peptide (e.g., an RGD peptide). By way of example, the targeting agent can be covalently linked to the polymer. In some embodiments, the targeting agent can be capable of binding to, or otherwise associating with, a target biological entity, e.g., a membrane component, a cell surface receptor, a prostate specific membrane antigen, or the like. In some embodiments, the targeting agent can cause the nanoparticles administered to a subject to become localized to a tumor, a disease site, a tissue, an organ, a type of cell, e.g., a cancer cell. In some embodiments, the targeting agent can be selected from the group of nucleic acid aptamers, growth factors, hormones, cytokines, interleukins, antibodies, integrins, fibronectin receptors, p-glycoprotein receptors, peptides and cell binding sequences.

In some embodiments, a radiopharmaceutical agent e.g., a radiotherapeutic agent, a radioimaging agent, or other radioisotope can be coupled to, associated with or incorporated in the polymer, e.g., embedded in the polymer.

In some embodiments, the process solvent is an organic solvent (or a mixture of two or more organic solvents). In some embodiments, the process solvent is capable of dissolving at least about 0.1%, or at least about 0.2%, by weight of the polymer at room temperature.

Some examples of suitable process solvents include, without limitation, acetone, ether, alcohol, tetrahydrofuran, 2-pyrrolidone, N-Methyl-2-pyrrolidone (NMP), dimethylformamide (DMF), dimethylacetamide (DMA), methyl acetate, ethyl formate, methyl ethyl ketone (MEK), methyl isobutyl ketone (MIBK), methyl propyl ketone, isopropyl ketone, isopropyl acetate, acetonitrile (MeCN) and dimethyl sulfoxide (DMSO).

In some embodiments, the anti-solvent can be an aqueous (water-based) solution, another solvent, a combination of a solvent and an aqueous solution, or a combination of one or more organic solvents. In some embodiments, the anti-solvent can be purified water. Some other examples of suitable anti-solvents include, without limitation, methanol, ethanol, n-propanol, isopropanol, n-butanol, ethyl ether, and water: ethanol (e.g., 50:50). In some cases, the anti-solvent can be a liquefied gas, such as carbon dioxide under adequate pressure.

In some embodiments, the anti-solvent can include a colloid stabilizer, e.g., to inhibit aggregation of the formed nanoparticles. Some examples of suitable colloid stabilizers include, without limitation, poly(vinyl alcohol) (PVA), Dextran and pluronic F68, poly(vinyl pyrrolidone), solutol, Tween 80, poloxamer, carbopol, poly-ethylene glycol (PEG), sodium dodecyl sulfate, poly($\epsilon$-caprolactone), peptides, and carbohydrates. Another example of a colloid stabilizers includes, without limitation, a PEG-lipid (e.g., PEG-ceramide, d-alpha-tocopheryl polyethylene glycol 1000 succinate, 1,2-Distearoyl-sn-Glycero-3-[Phospho-rac-(1-glycerol)] or lecithin). In some embodiments, the PVA is from about 5 to about 45 kDa, for example, the PVA is from about 5 to about 30 kDa (e.g., the PVA is from about 5 to about 20 kDa), and up to about 98% hydrolyzed (e.g., about 85% hydrolyzed). In some embodiments, the viscosity of the PVA (4% PVA in water), measured by utilizing the falling ball method, is in a range of about 2.5 to about 6.5 mPasec (e.g., in a range of about 2.5 to about 3.5 mPasec at a temperature of about 20° C.). In some embodiments, the viscosity of the PVA (4% PVA in water), measured by utilizing the falling ball method, is in a range of about 3.4 to about 4.6 mPasec.

In some embodiments, the polymer solution can have one or more additive molecules. As discussed above, in some embodiments, the additive molecules are embedded in the polymer prior to formation of the polymer solution. In other embodiments, the additive molecules can become embedded in the polymeric nanoparticles during the precipitation process. For example, in some embodiments, the additive molecule can be conjugated to the polymer, e.g., via covalent bonding, and the conjugated polymer can be dissolved in a process solvent to form the polymer solution. In other cases, the additive molecules can be present in the polymer solution without being conjugated to the polymer and become subsequently trapped in polymeric nanoparticles during the precipitation process.

By way of example, the additive molecules can be a therapeutic, or an imaging agent or a combination of therapeutic and imaging agents. Some examples of suitable therapeutic agents include, without limitation, anti-neoplastic agents, anti-inflammatory agents, cardiovascular active agents, and anti-metabolites.

In some embodiments, the imaging agent can be coupled, e.g., conjugated to the polymer, for incorporation in the nanoparticles. In other embodiments, the imaging agent can be coupled, e.g., via a chelating agent, to a therapeutic agent, which is in turn coupled, e.g., conjugated, to the polymer. The imaging agents can include, e.g., radioactive, non-radioactive, or fluorescent labels. Some examples of imaging agents include, without limitation, radiopharmaceuticals such as Technetium Bicisate, Ioxaglate, and Fluorodeoxyglucose, label-free Raman imaging agents, encapsulate MRI contrast agent Gd-DTPA, and rhodamine 6G as a fluorescent agent. In some embodiments, the imaging agent can be radiolabeled docetaxel (e.g., 3H-radiolabeled or 14C-radiolabeled docetaxel), or radiolabeled paclitaxel.

Referring again to the flow chart of FIG. 1, the nanoparticles formed in the precipitation process can be collected, e.g., as a suspension (step F). For example, the formed nanoparticles entrained in a mixture of anti-solvent and process solvent (in many cases, mostly anti-solvent) flowing downstream from the static mixer can be introduced into a tank, e.g., a tank containing a liquid, e.g., deionized water. A suspension of the nanoparticles can then be collected from the tank.

The collected nanoparticles can be subjected to a variety of processes, which may be conducted aseptically, to yield aqueous or non-aqueous solutions, dispersions or powders. For example, as discussed in more detail below, a concentrated suspension of the nanoparticles can be lyophilized to yield a powder containing the nanoparticles, e.g., a sterile powder. In some applications, such a sterile powder of the nanoparticles can be subsequently reconstituted into sterile injectable solutions or dispersions.

For example, with continued reference to the flow chart of FIG. 1, the collected suspension containing the nanoparticles can be diafiltered and concentrated (step G). By way of example, the suspension containing the nanoparticles can be diafiltered, e.g., to remove at least a portion of the process solvent, the colloid stabilizer or other additives added to the anti-solvent. In some embodiments, the diafiltration (also known in the art as crossflow filtration) can be performed in multiple steps. In some such embodiments, the nanoparticles can be washed, e.g., by using deionized water, between successive diafilteration steps. Further, in some embodiments the diafilteration is conducted preferably in a continuous fashion, i.e., by adding wash solution during the diafiltration process.

In some embodiments in which the polymeric nanoparticles include therapeutic and/or imaging agents, the concentration of these agents can be monitored (step H) while the suspension containing the nanoparticles is being concentrated. While in some cases such monitoring is performed continuously, in other cases it can be performed at multiple discrete times. By way of example, high pressure liquid chromotagraphy (HPLC) can be employed to assay the suspension as the volume of the anti-solvent and process solvent mixture is reduced.

With continued reference to the flow chart of FIG. 1, in this exemplary embodiment, a lyoprotectant is added to the concentrated suspension of the nanoparticles to protect the nanoparticles from damage and/or to retard permanent aggregation of the nanoparticles when subsequently subjected to lyophilization. The lyoprotectant can also facilitate the resuspension of the nanoparticles. Some examples of suitable lyoprotectants include, without limitation, a derivatized cyclic oligosaccharide, e.g., a derivatized cyclodextrin, e.g., 2 hydroxy propyl-$\beta$cyclodextrin, e.g., partially etherified cyclodextrins (e.g., partially etherified $\beta$ cyclodextrins) disclosed in U.S. Pat. No. 6,407,079, the contents of which are incorporated herein by this reference.

In step (J), the concentrated suspension containing the nanoparticles and the lyoprotectant can then be stored in one or more suitable vessels, e.g., vials, and lyophilized in a manner known in the art (step K). The vials can then be sealed to protect the nanoparticles from spoilage. By way of example, the lyophilization can be achieved by initially freezing the concentrated suspension followed by a primary drying phase in which the ambient pressure to which the concentrated suspension is subjected is lowered (e.g. to a few millibars) while supplying enough heat to cause sublimation of frozen liquid, mostly frozen water in many implementations at this stage. In a secondary drying phase, unfrozen liquid (e.g., water molecules), if any, can be removed by raising the temperature above that in the primary. In some embodiments, upon completion of the freeze-drying process, an inert gas, such as nitrogen, can be introduced into the vessel containing the lyophilized nanoparticles prior to sealing the vessel.

As discussed above, the use of a static mixer in generating a mixed flowing stream of an anti-solvent into which a polymer solution is introduced for generating nanoparticles advantageously allows operating the precipitation process at a variety of anti-solvent, and polymer solution, flow rates. It has been discovered that the anti-solvent flow rate and/or the polymer solution flow rate can be adjusted to control the average particle size of the formed nanoparticles in a predictable manner. Hence, in another aspect, the invention provides a method for controlling particle size of nanoparticles formed by precipitation.

Figure 3:
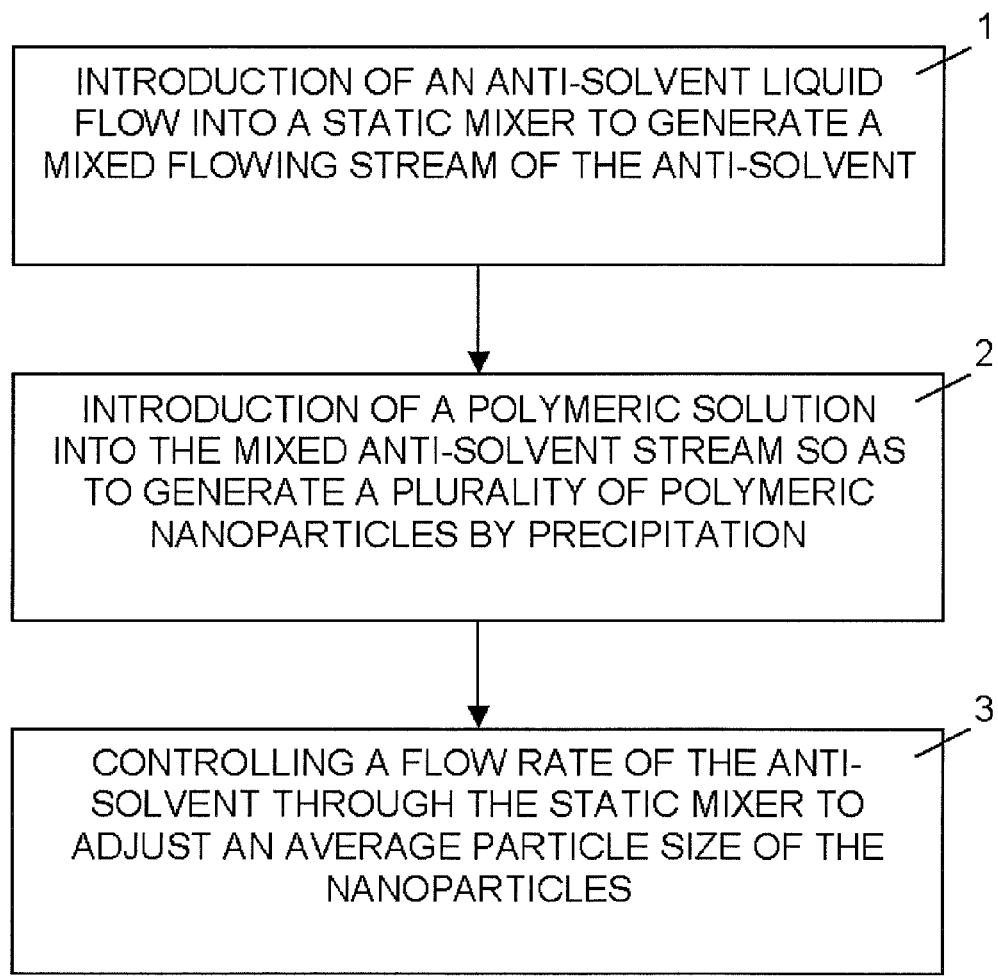
FIG. 3 is a flow chart depicting various steps according to an exemplary embodiment of the invention for controlling particle size of nanoparticles formed by nanoprecipitation, FIG. 4A schematically depicts a device according to an exemplary embodiment of the invention for forming nanoparticles, FIG. 4B schematically depicts an alternative implementation of the device of FIG. 4A, FIG. 5A schematically depicts a device according to another embodiment for generating nanoparticles in accordance with the teachings of the invention, FIG. 5B schematically depicts a device according to another embodiment for generating nanoparticles in accordance with the teachings of the invention, FIG. 5C schematically depicts a device according to another embodiment for generating nanoparticles in accordance with the teachings of the invention, FIG. 5D schematically depicts a device according to another embodiment for generating nanoparticles in accordance with the teachings of the invention, FIG. 5E schematically depicts a device according to another embodiment for generating nanoparticles in accordance with the teachings of the invention, FIG. 6A schematically depicts a device according to another embodiment for generating nanoparticles in accordance with the teachings of the invention in which a plurality of static mixer units are employed, FIG. 6B schematically depicts a device according to an alternative implementation of the device of FIG. 6A, FIG. 6C schematically depicts a device according to another embodiment of the invention, FIG. 7 schematically depicts a system according to an exemplary embodiment of the invention for generating nanoparticles, FIG. 8A schematically depicts a device according to an embodiment of the invention for generating nanoparticles, which employs an injector for injecting a polymer solution into a mixed flowing stream of an anti-solvent, FIG. 8B schematically depicts a device according to another embodiment of the invention for generating nanoparticles, which employs an injection system disposed across a conduit through which a mixed stream of an anti-solvent flows to inject a polymer solution into the anti-solvent flow.

For example, with reference to the flow chart of FIG. 3, in such a method, an anti-solvent flow is introduced into a static mixer to generate a mixed flowing stream of the anti-solvent (step 1). A polymer solution is then introduced into the mixed flowing stream of the anti-solvent so as to provide a plurality of nanoparticles by precipitation (step 2). The flow rate of the anti-solvent through the static mixer is controlled (step 3) so as to adjust an average particle size of the nanoparticles.

By way of example, the flow rate of the anti-solvent through the static mixer can be changed in a range of about 20 ml/min to about 2000 ml/min so as to vary the average particle size in a range of about 50 nm to about 200 nm.

In some embodiments the flow rate of the anti-solvent is changed, while maintaining the flow rate of the polymer solution substantially constant, so as to adjust the average particle size of the nanoparticles. For example, in some embodiments that utilize high ratios of the flow rate of the anti-solvent relative to that of the polymer solution, e.g., ratios of 10:1 or higher, the average particle size can be controlled by adjusting only the anti-solvent flow rate. In other embodiments, the polymer solution flow rate is changed, while maintaining the flow rate of the anti-solvent substantially constant, so as to adjust the average particle size of the nanoparticles. Alternatively, both the anti-solvent flow rate and that of the polymer solution can be concurrently changed so as to adjust the average particle size of the nanoparticles.

In some embodiments, the concentration of the polymer in the polymer solution and/or the concentration of the colloid stabilizer added to the anti-solvent can be changed so as to adjust the average particle size of the nanoparticles.

The above processes for generating nanoparticles with controlled average particle sizes and a low polydispersity index find a variety of applications, such as nanopharmaceutical therapeutic applications. For example, they can be employed to fabricate nano-scale drug delivery systems for selectively targeting disease tissue. For example, polymeric nanoparticles embedded with therapeutic agents can be formed for selectively targeting diseases and disorders such as oncological diseases, autoimmune diseases as well as cardiovascular diseases.

The ability to predictably control the average particle size and particle size distribution afforded by the methods of the invention allows optimizing selective delivery of such therapeutic nanoparticles. For example, the average particle size of the nanoparticles can be selected to allow their preferential accumulation in cancerous tumors via their passage through leaky blood vessels of such tumors. Further, a narrow size distribution of the nanoparticles can be employed to ensure that the therapeutic nanoparticles can effectively target cancerous tumors.

Further, in some embodiments, polymeric nanoparticles can be employed for sustained drug delivery. For example, in some embodiments, a therapeutic agent can be entrapped within a nanoparticle formed of a biodegradable polymer. As the polymer coating is degraded, the entrapped agent can be released into a subject to whom the nanoparticles have been delivered.

In addition, the nanoparticles can be formed so as to be masked from a host's immune system, thereby exhibiting reduced immunogenicity and antigenecity. By way of example, the polymer nanoparticles can be PEGylated to extend their circulation time in a host. PEGylated nanoparticles can evade a subject's immune system, and PEGylated chemotherapeutic nanoparticles can lower the toxicity of the therapeutic agent and reduce unwanted side effects.

In some embodiments, the above processes for generating polymeric nanoparticles can allow controlling the amount of a therapeutic or an imaging agent that can be loaded onto a nanoparticle (e.g., coupled to, associated with or incorporated into the nanoparticles), and controlling the release rate of such an agent upon introduction of the nanoparticle into a subject. For example, the amount of a therapeutic agent that can be loaded onto a nanoparticle can vary based on the degree of branching exhibited by a linker attached to the polymer from which the nanoparticle is formed and to which the agent can be coupled.

The applications of nanoparticles, and particularly polymeric nanoparticles, formed in accordance with the teachings of the invention are not limited to therapeutic applications. For example, the nanoparticles can also be employed in imaging applications.

The polymeric nanoparticles can be delivered to a subject in a variety of ways. For example, the nanoparticles can be combined with suitable supplemental additives, such as water, ethanol, propyleneglycol, polyethyleneglycol, glycerol, vegetable oils, and ethyloleate, for parenteral injection into a subject. In some embodiments, the nanoparticles can be administered orally, e.g., via encapsulation of lyophilized nanoparticles using known excipients. In some embodiments, the nanoparticles can be administered by inhalation, e.g., via nebulization, propellant or a dry powder device. In some embodiments, the nanoparticles can be administered mucosally (e.g., via vaginal or rectal mucosa). In some embodiments, the nanoparticles can be applied in a topical form to a subject's tissue. In some embodiments, the nanoparticles can be administered ophthalmically.

Figure 4A:
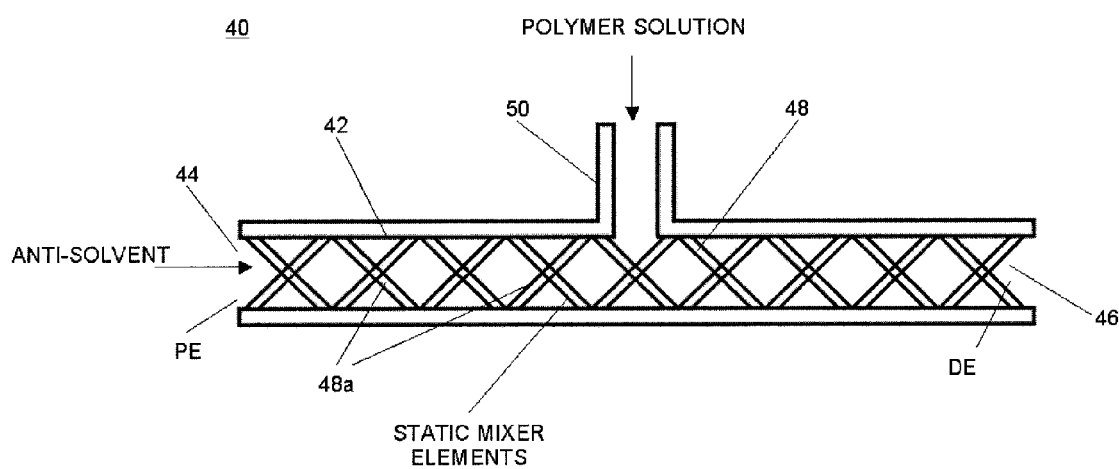

FIG. 4A schematically depicts a device 40 according to an embodiment of the invention for generating polymeric nanoparticles. The device 40 includes a conduit 42, e.g., a hollow tube, that extends axially from a first input (inlet) port 44, through which a fluid, e.g., an anti-solvent, can be introduced into the conduit, and an output (outlet) port 46. A static mixer 48 is disposed in the conduit to receive the fluid entering the conduit through the input port 44. The exemplary static mixer 48 extends from a proximal end (PE) to a distal end (DE), and includes a plurality of stationary baffles 48a that cause mixing of the fluid as it flows through the mixer. Different types of static mixers can be employed in the device 40. By way of example, some suitable static mixers are disclosed below in the Examples section. By way of further examples, static mixers disclosed in U.S. Pat. Nos. 3,286,992 and 4,511,258 entitled, respectively, "Mixing Device," and "Static Material Mixing Apparatus," which are herein incorporated by reference in their entirety, can be employed. By way of another example, in some embodiments, static mixers marketed by Chemineer, Inc. of Ohio, U.S.A. under the trade designation Kenics static mixers can be employed.

The device 40 further includes a second input port 50 through which a second fluid (e.g., another fluid such as a polymer solution as discussed below) can be introduced into the fluid flowing axially along the conduit 42 through the static mixer 48. In this embodiment, the second input port 50 is disposed at an intermediate location between the proximal end (PE) and the distal end (DE) of the static mixer 48.

While in this embodiment the second port is configured to introduce a stream of fluid, e.g., a polymer solution, into the fluid, e.g., anti-solvent, flowing axially through the conduit at an angle of about 90 degrees relative to the axial flow direction, in other embodiments the second port can be configured such that the direction of the flow of the second fluid would intersect the axial flow direction at an angle other than 90 degrees.

Figure 4B:
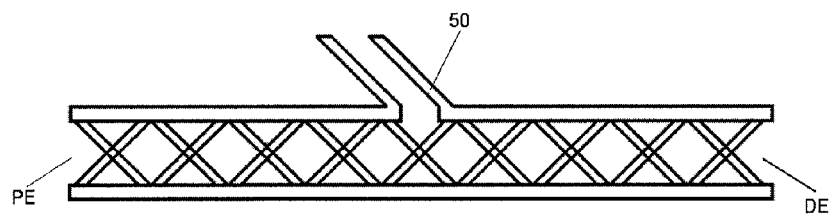

By way of example, FIG. 4B schematically depicts another embodiment of a device in which the second input port 50 is configured to introduce a fluid into the conduit along a direction that forms a non-orthogonal angle with the direction of axial flow.

In use, an anti-solvent flowing stream is established through the conduit 42 via the input port 44, e.g., causing the anti-solvent to flow from a reservoir (not shown) into the conduit, for example, via pumping, as discussed in more detail below. The static mixer causes mixing of the flowing anti-solvent so as to provide a mixed flowing stream of the anti-solvent before the stream reaches the second input port 50. Once a mixed flowing stream of the anti-solvent has been established, a polymer solution can be introduced into the anti-solvent stream via the second input port 50 (e.g., by causing the polymer solution to flow from a reservoir (not shown) into the conduit, for example, via pumping, as discussed in more detail below).

As discussed above, the contact of the polymer solution with the anti-solvent results in precipitation of the polymer into a plurality of polymeric nanoparticles that are carried by the stream of the anti-solvent away from the static mixer. The formed nanoparticles can then be collected as a suspension in a mixture of anti-solvent and the process solvent. As discussed above, in many embodiments, the rate of flow of the anti-solvent through the conduit 42 is substantially greater than the flow rate of the polymer solution into the conduit, e.g., by a factor of about 10 or more. Hence, in such embodiments, the nanoparticles are surrounded primarily by the anti-solvent—including any additive(s) such as a colloid stabilizer added to the anti-solvent—as they move down the conduit to a collection device—though the collection device receives typically the process solvent and, in some cases additives added to the process solvent, as well. Further, in many embodiments, the flow rate of the anti-solvent is sufficiently fast to ensure that the polymer solution entering the conduit would interact with a fresh batch of anti-solvent that is substantially free of process solvent and polymeric material that had previously entered the conduit.

Figure 5A:
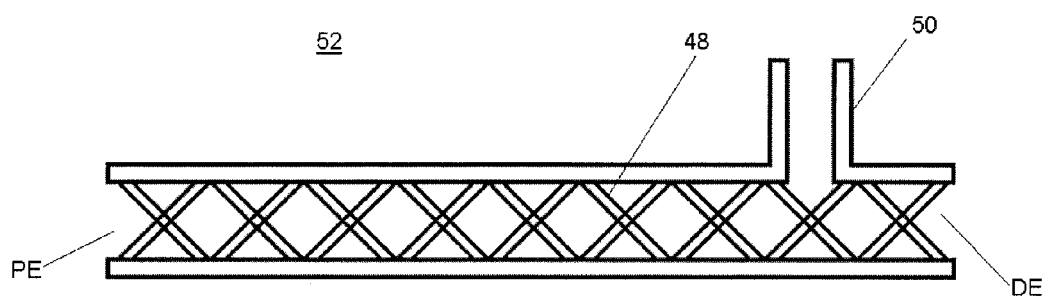

While in the above device 40 the second input port is positioned at an intermediate location relative to proximal and distal ends of the static mixer, in other embodiments the second input port can be positioned in proximity to the proximal end or the distal end of the static mixer. By way of example, FIG. 5A schematically depicts a device 52 according to an alternative implementation of the above device 40 for generating nanoparticles in which the second input port 50 is positioned in proximity to the distal end (DE) of the static mixer. For example, the input port 50 can be offset from the distal end of the mixer by one or two mixing elements.

Figure 5B:
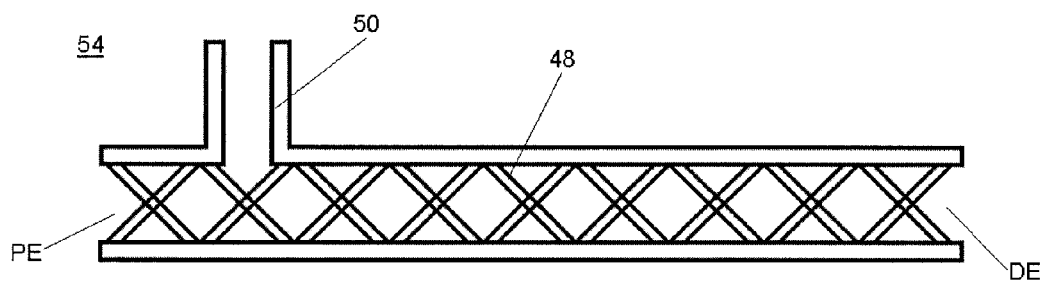
Figure 5C:
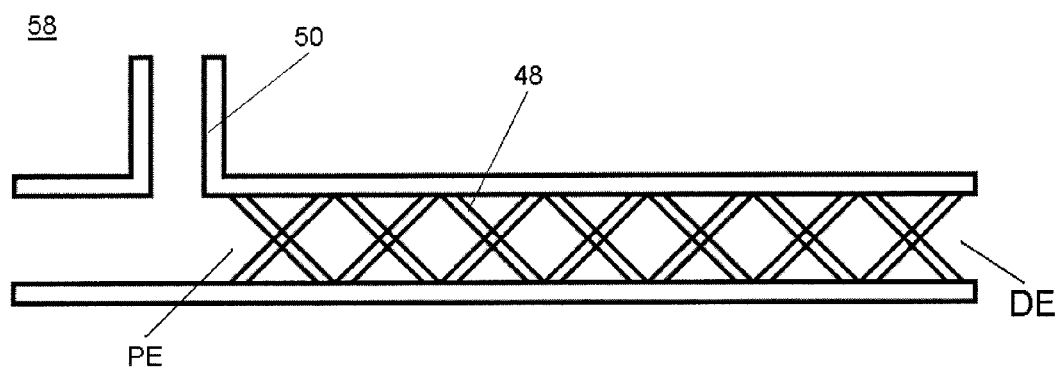

By way of another example, FIG. 5B schematically depicts a device 54 according to another alternative implementation of the above device 40 in which the second input port 50 is positioned in proximity to the proximal end (PE) of the static mixer, e.g., offset by one or two mixing elements from the proximal end. In some embodiments, the static mixer is preferably selected to generate a mixed flowing stream of the anti-solvent over a short length of the mixer. In some embodiments the static mixer can be chosen such that its mixing effect on the anti-solvent flow would even be present slightly upstream from the proximal end of the mixer. In such embodiments, as shown schematically in FIG. 5C, the second input port can be positioned slightly upstream from the static mixer but sufficiently close to its proximal end such that the incoming polymer solution would interact with a mixed flowing stream of the anti-solvent.

Figure 5D:
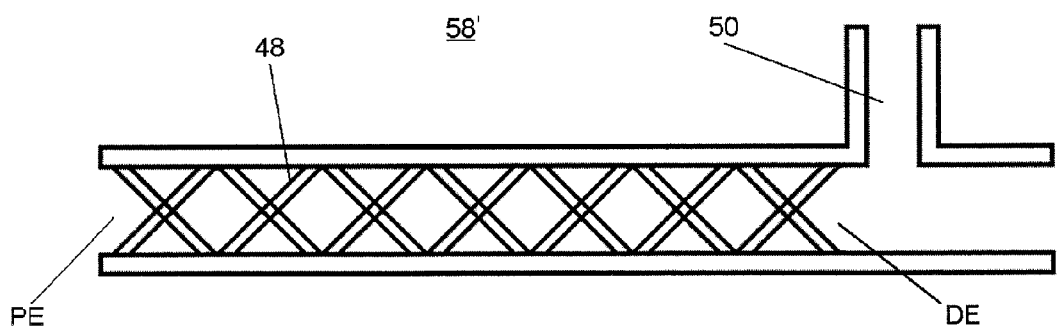

The static mixer can also be chosen such that its mixing effect on the anti-solvent flow is present downstream from the distal end of the mixer. In such embodiments, as shown schematically in FIG. 5D, the second input port 50 of a device 58' can be positioned slightly downstream from the static mixer 48 but sufficiently close to its distal end DE (e.g., within approximately 1-2 mixing element lengths) such that the incoming polymer solution would interact with a mixed flowing stream of the anti-solvent.

Figure 5E:
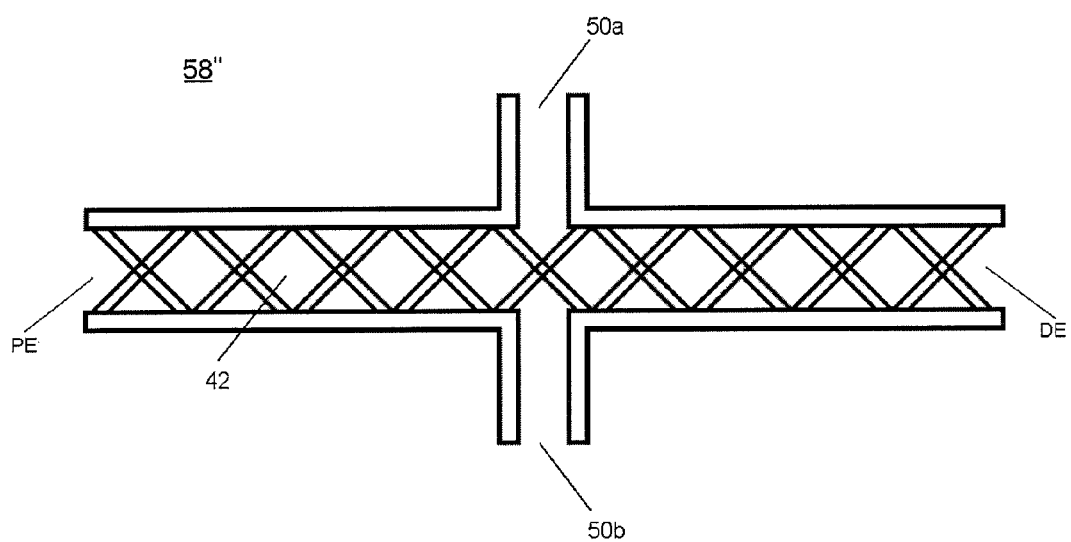

In some embodiments, a plurality of input ports for introducing the polymer solution into a mixed flowing stream of anti-solvent can be provided. For example, as shown in FIG. 5E, a device 58" can include a plurality of polymer solution input ports 50a, 50b on opposite sides of the conduit 42. In other embodiments, the plurality of polymer solution input ports can be located on the same side of the conduit and/or can be spaced at various intervals from each other along the length of the conduit 42.

Figure 6A:
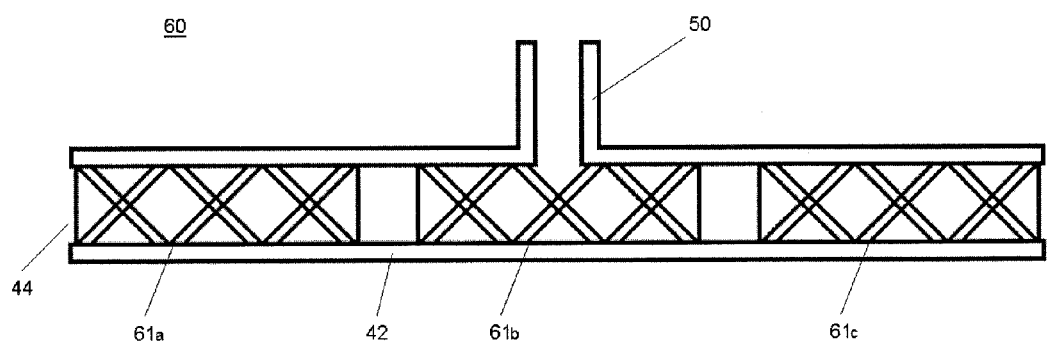
Figure 6B:
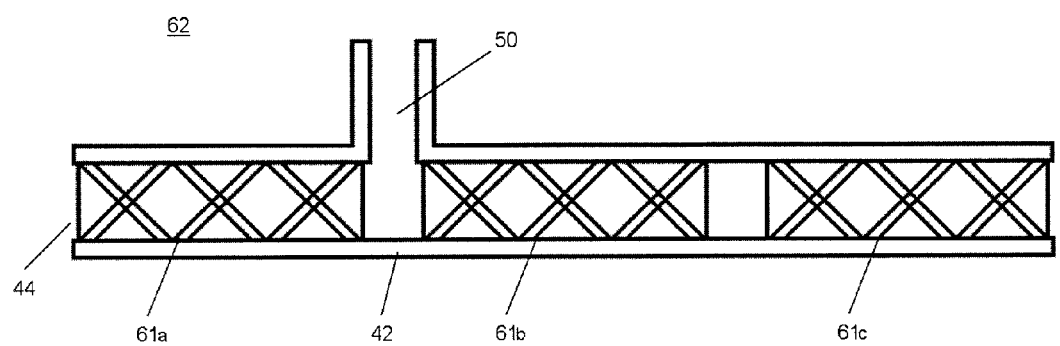

In other embodiments, rather than utilizing a single static mixer unit, a plurality of static mixer units can be employed. For example, FIG. 6A schematically depicts a device 60 according to an embodiment of the invention that, similar to the above device 40, includes a conduit 42 for receiving a flowing stream of an anti-solvent through a first input port 44 as well as a second input port 50 for introducing a stream of a polymer solution into the mixed flowing stream of the anti-solvent. In device 60, a plurality of static mixer units 61a, 61b, 61c are disposed within the conduit 42 to cause mixing of the flowing anti-solvent. The static mixer units are disposed in series, preferably in staggered orientation relative to one another. While FIG. 6A illustrates the input port 50 as being positioned roughly in the center of one of the static mixer units 61b, in other embodiments the input port 50 can be positioned differently. For example, in some embodiments, as illustrated in FIG. 6B, a device 62 can include a second input port 50 that is positioned between adjacent static mixer units 61a, 61b so as to deliver the polymer solution to into a gap between those units.

Figure 6C:
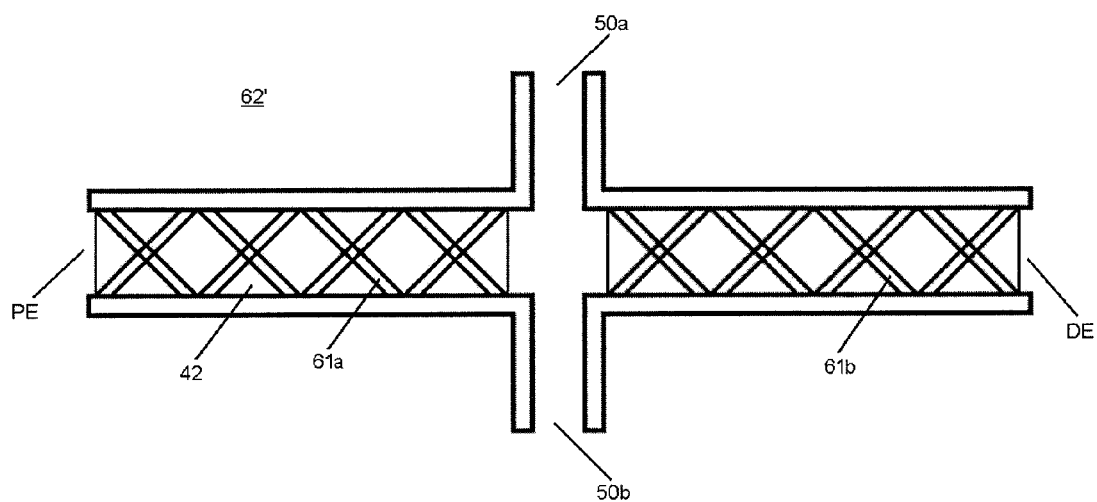

FIG. 6C schematically illustrates a device 62' according to another embodiment of the invention that includes a conduit 42 in which static mixer units 61a, 61b are disposed. The device 62' includes two input ports 50a, 50b, which are positioned on opposite sides of the conduit 42, for the introduction of a polymer solution into the conduit. The static mixer units are separated from one another so as to provide a gap in the vicinity of the input ports 50a,50b such that a polymer solution can be introduced through the gap into the conduit.

Figure 7:
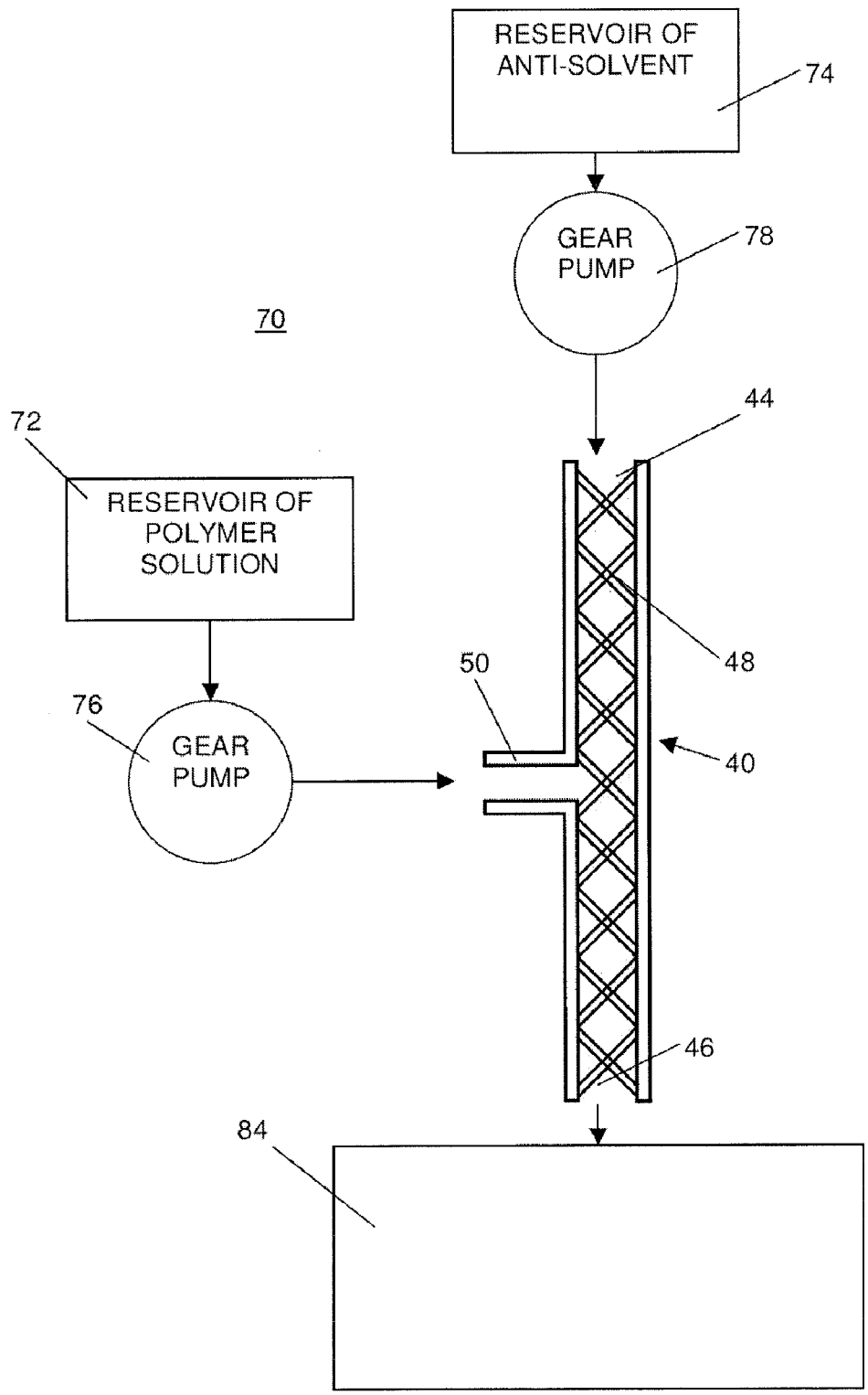

FIG. 7 schematically depicts a system 70 according to an embodiment of the invention for generating polymeric nanoparticles in which any of the above devices 40, 52, 54, 56, 58, 58', 58", 60, 62 in any of their various implementations can be incorporated. The system 70 includes a reservoir 72 for storing a polymer solution and another reservoir 74 for storing an anti-solvent, such as a mixture of deionized water and a colloid stabilizer. A device 78, e.g., a gear pump, is fluidly connected at its input to the reservoir 74 and is fluidly coupled at its output to first input port 44 of the device 40 to cause a flow of the anti-solvent from the reservoir into the conduit 42. A static mixer 48 is disposed within the conduit 42. As discussed above, the flow of the anti-solvent stream through the static mixer generates a mixed flowing stream of the anti-solvent.

Another device 76, e.g., another gear pump, is fluidly connected at its input to the reservoir 72 and at is output to the second input port 50 of the device 40 to cause a flow of the polymer solution from the reservoir 72 via the second port into the mixed flowing stream of the anti-solvent to cause precipitation of the polymer into a plurality of polymeric nanoparticles. As discussed above, although in many embodiments the flow rate of the anti-solvent is substantially greater than that of the polymer solution, e.g. by a factor of 10, a variety of anti-solvent and polymer solution flow rates can be employed.

In this embodiment, both of the devices 76 and 78 are variable pumps that can adjust the flow rate of the anti-solvent and the polymer solution, respectively, for introduction into the device 40. By way of example, in this implementation, the device 78 can adjust the flow rate of the anti-solvent in a range of about 20 ml/min to about 2000 ml/min, and the device 76 can adjust the flow rate of the polymer solution in a range of about 4 ml/min to about 200 ml/min, or, in some embodiments, in a range of about 5 ml/min to about 100 ml/min. As noted above, in some embodiments, the devices 76 and 78 are gear pumps. An example of suitable gear pump is a pump marketed by Cole-Parmer Instrument Company of Illinois, U.S.A. under the trade designation Ismatec.

The output port 46 of the device 40 is in fluid communication with a collection vessel 84. The formed nanoparticles are entrained in a fluid stream comprising a mixture of the anti-solvent and the process solvent (in many cases the anti-solvent is the major component of the fluid stream) that carries the nanoparticles via the output port 46 into the collection vessel 84, which may contain a liquid, e.g., deionized water. In some embodiments, the collection vessel is not pre-filled with a liquid. A suspension containing the nanoparticles can be collected from the collection vessel to be concentrated and in some embodiments lyophilized, e.g., in a manner discussed above.

As discussed above, it has been discovered that the use of a static mixer to cause mixing of the anti-solvent stream allows generating nanoparticles with a low polydispersity index over a wide range of flow rates, e.g., a polydispersity index equal to or less than about 0.25 (e.g., in a range of about 0.05 to about 0.1). In addition, the flow rate can be adjusted to obtain a desired average particle size. In this embodiment, the variable pump 78 allows changing the flow rate of the anti-solvent to "dial" the average particle size of the nanoparticles generated via nanoprecipitation.

Figure 8A:
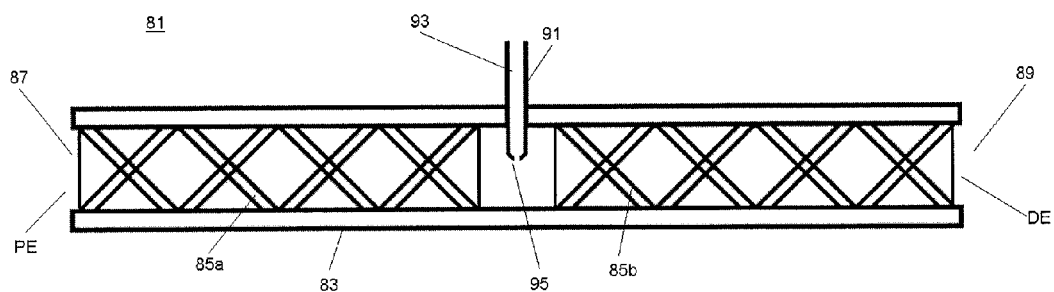

In some embodiments, one or more injectors can be employed to introduce the polymer solution into the mixed flowing stream of the anti-solvent. By way of example, FIG. 8A schematically shows a device 81 according to such an embodiment of the invention for generating nanoparticles, which includes a conduit 83 in which two static mixer units 85a and 85b are disposed. Similar to the previous embodiments, the conduit 83 includes an input port 87 through which a fluid, e.g., anti-solvent, can be introduced into the conduit and an output port 89 through which the fluid exits the conduit. In this embodiment, an injector 91 is coupled to the conduit at an intermediate location between the static mixer units. The injector 91 includes an inlet port 93 for receiving a fluid, e.g., a polymer solution, and an output nozzle 95 that is positioned within the conduit and is configured to inject the fluid into the mixed flowing stream of the anti-solvent. Although the illustrated nozzle faces downward (it is aimed substantially perpendicular to the axial direction of the anti-solvent flow), the nozzle can also be aimed at other angles with respect the direction of the anti-solvent flow. For example, the nozzle can include a 90 degree bend such that it is aimed parallel to the direction of the anti-solvent flow towards the mixer's distal end.

Figure 8B:
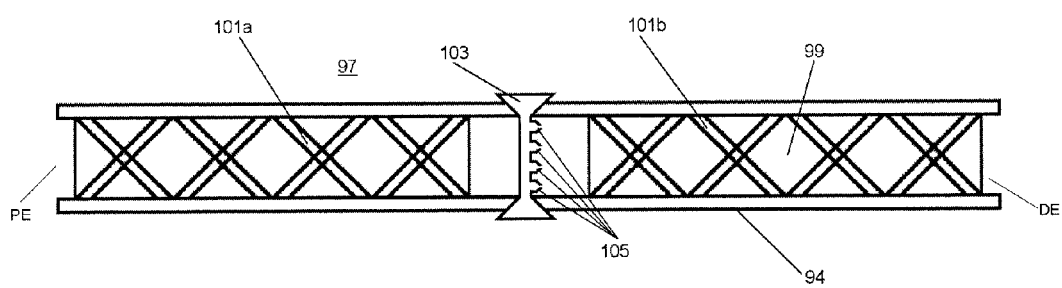

FIG. 8B schematically depicts another device 97 according to the teachings of the invention that employs an injection system for injecting a polymer solution into a mixed flowing stream of the anti-solvent. The device 97 includes a conduit 99 in which a two static mixer 101a and 101b are disposed. An injection system 103 extends across the conduit within a gap between the two static mixer units. The injection system includes a plurality of injection nozzles 105 that are configured to inject a polymer solution in a downstream direction and with sufficient velocity such that the polymer solution would be introduced into a mixed flowing stream of an anti-solvent through the mixer from mixer's proximal end to its distal end.

EXAMPLES

The following examples are provided for further elucidation of various aspects of the invention. The examples are intended only for illustrative purposes and do not necessarily represent optimal ways of practicing the invention and/or optimal results that can be obtained.

Figure 9:
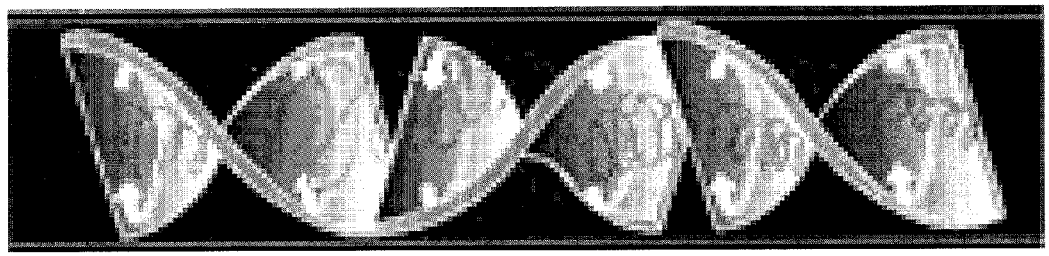
FIG. 9 shows a helical static mixer employed in some prototype devices based on the teachings of the invention for generating nanoparticles, FIGS. 10A and 10B provide two views of a structured-packing mixer marketed by Sulzer Chemtech USA, Inc. of Oklahoma, U.S.A. under the trade designation Sulzer SMX, which was employed in some prototype devices based on the teachings of the invention for generating nanoparticles.
Figure 10A:
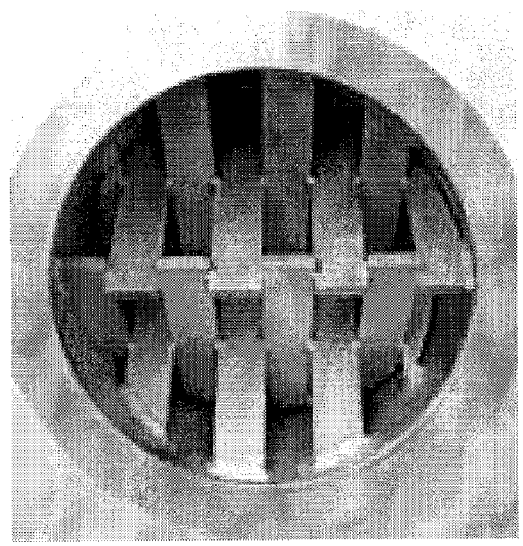
Figure 10B:
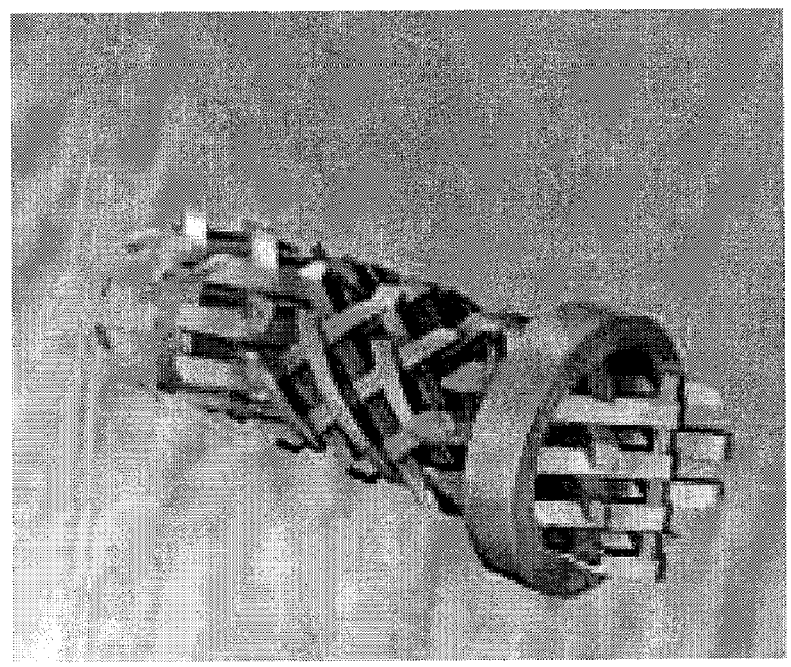

A prototype system based on the system shown in FIG. 7 above was assembled to generate polymeric nanoparticles in accordance with the above teachings, as discussed in the following examples. In some of the following examples, a helical static mixer similar to that shown in FIG. 9 marketed by Cole-Parmer Instrument Company of Illinois, U.S.A. was employed. The helical static mixer includes alternating left and right-hand twists that cause a fluid flowing through the mixer to move from the wall of a conduit in which the mixer is disposed to the center of the mixer and from the center to the wall in an alternating fashion. In some other examples, a static mixer known as a "structured-packing mixer" marketed by Sulzer Chemtech USA, Inc. of Oklahoma, U.S.A. under the trade designation Sulzer SMX, shown in FIGS. 10A and 10B, was employed. This mixer includes a lattice of mixing elements that is oriented at 45 degrees relative to the direction of the flow.

Figure 11A:
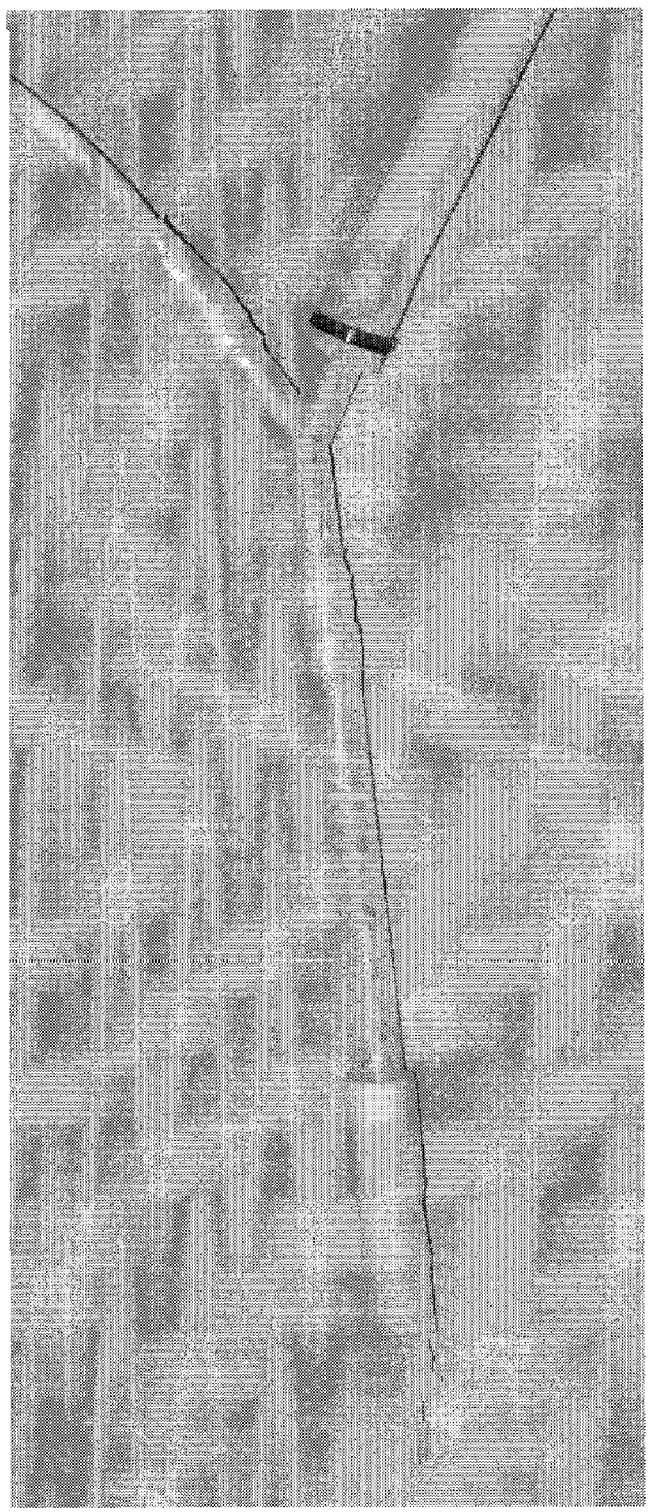
FIG. 11A shows a prototype device according to an embodiment of the invention, which was employed to generate polymeric nanoparticles.

At least two prototype devices were constructed:

I. A 5 mm internal diameter (ID) helical mixer device was constructed by inserting a 5 mm OD polyacetal helical mixer (Cole-Parmer) into a 5 mm ID polypropylene tube fitted with a barbed polypropylene "Y" fitting on one end. (as shown in FIG. 11A). The mixer was extended through one of the arms of the "Y" fitting. The aqueous phase (i.e., anti-solvent) was directed via ¼ inch tubing through the mixer-containing arm. The organic phase (i.e., polymer solution) was directed via ⅛ inch tubing through the other (empty) arm. A ¼ inch to ⅛ inch reducer was connected to the bottom port to provide a slight back pressure.

Figure 11B:
FIG. 11B shows a prototype device according to an embodiment of the invention, which was employed to generate polymeric nanoparticles.

II. An 8 mm ID modified SMX mixer device was constructed by modifying a standard ¼ inch Sulzer (Sulzer Chemtech USA, Tulsa, Okla.) SMX mixer with an ⅛ inch ID side entry port midway along the static mixer length. The mixer was fabricated from 316L stainless steel mixer (FIG. 11B). It was 3 inches long with an 8 mm bored ID and contained 8 SMX type elements. The mixer was configured such that the aqueous phase flowed through the mixer main body while the organic phase entered the side port.

Example 1

The following process was used to characterize the effect of organic and aqueous flowrates on average particle size and polydispersity using the prototype helical mixing device depicted in FIG. 11A.

2 grams of 5050 PLGA (5050DLG 1AP, Mw=6.4 kD, Mn=2.9 kD, Lakeshore Biomaterials, Birmingham, Ala.) were dissolved in 158 grams of acetone and sonicated for 30 seconds at room temperature. Separately, 10 grams of poly vinyl alcohol (PVA) (80% hydrolyzed, Mw 9-10 kD, Aldrich, St Louis, Mo.) was dissolved in 2 kilograms of water at room temperature. Each solution was translucent and visually free of undissolved material.

The organic and aqueous phases were transferred to glass reservoirs, the bottom outlet of each was connected to pre-calibrated magnetically driven gear pumps (Ismatec, Cole-Parmer) via flexible tubing to the respective ports of the helical mixer device. A particle size sample was collected by first initiating the aqueous flow, then the organic flow to predetermined flow rates. After a few moments of flushing, a small suspension sample was collected at the tubing outlet and then pumps were turned off in reverse order. The pump settings were then readjusted and a subsequent particle size sample taken. At the conclusion of the experiment, each sample particle size was measured via Malvern Zetasizer Model Nano S (Malvern Instruments, Southborough, Mass.). In most cases each particle size measurement was conducted in duplicate and the results averaged.

Total flow rates in the range of about 25 to 500 ml/min with the organic phase relative to the aqueous phase flow rate (O:W) ratios of 1:5 and 1:10 were employed and the results shown below:

TABLE 1

| O:W Ratio | Qo (ml/min) | Qw (ml/min) | Qt (ml/min) | Z-Avg (nm) | PdI | D(v)50 (nm) | D(v)90 (nm) | D(v)10 (nm) |
|---|---|---|---|---|---|---|---|---|
| 1:5 | 73.0 | 365.0 | 438.0 | 84 | 0.089 | 68 | 109 | 47 |
|  | 60.0 | 301.0 | 361.0 | 94 | 0.052 | 82 | 122 | 59 |
|  | 47.0 | 237.0 | 284.0 | 102 | 0.073 | 90 | 138 | 63 |
|  | 34.3 | 172.0 | 206.3 | 111 | 0.093 | 97 | 156 | 67 |
|  | 21.5 | 107.4 | 128.9 | 123 | 0.059 | 112 | 175 | 77 |
|  | 12.9 | 64.4 | 77.3 | 140 | 0.072 | 131 | 211 | 86 |
|  | 4.3 | 21.5 | 25.8 | 180 | 0.065 | 183 | 268 | 126 |
| 1:10 | 46.4 | 463.5 | 509.9 | 87 | 0.082 | 71 | 114 | 48 |
|  | 38.6 | 386.5 | 425.1 | 92 | 0.071 | 78 | 121 | 54 |
|  | 30.1 | 300.0 | 330.1 | 98 | 0.091 | 81 | 134 | 55 |
|  | 21.5 | 214.0 | 235.5 | 110 | 0.076 | 92 | 157 | 62 |
|  | 12.9 | 128.0 | 140.9 | 121 | 0.066 | 110 | 173 | 75 |
|  | 4.3 | 42.9 | 47.2 | 152 | 0.061 | 147 | 232 | 97 |

In the above table and the tables that follow, $Q_o$ and $Q_w$ refer to flow rates of the organic and the aqueous phases, respectively. $Q_t$ refers to the total flow rate. Dv50 is defined as the particle size below which the sizes of 50% of the particles lie, Dv90 is defined as the particle size below which the sizes of 90% of the particles lie, and Dv10 is defined as the particle size below which the sizes of 10% of the particles lie.

The polydispersity index remains less than about 0.1 over the entire tested flow rate range.

Figure 12:
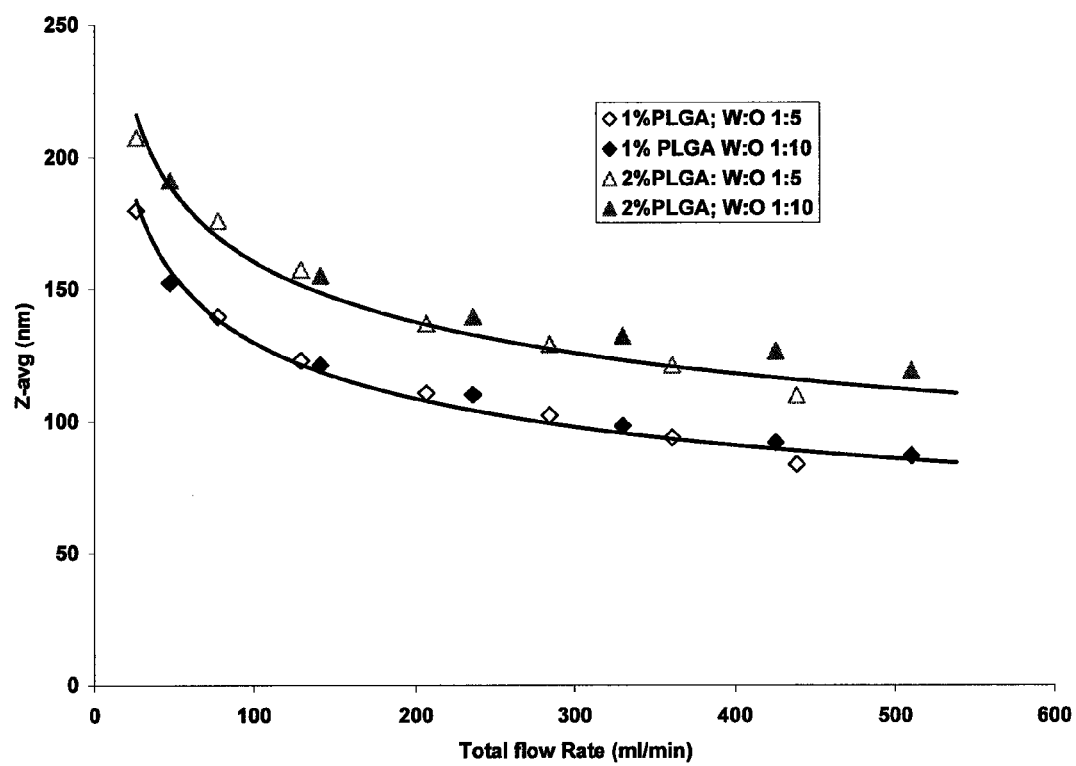
FIG. 12 presents data corresponding to $Z_{ave}$ as a function of total flow rate for nanoparticles generated in a prototype device according to the teachings of the invention.

FIG. 12 presents data corresponding to $Z_{ave}$ as a function of the total flow rate, indicating that the average particle size decreases as the flow rate increases from about 25 ml/min to about 500 ml/min. At flow rates less than about 200-300 ml/min, average particle size decreases at a much faster rate than flow rates greater than 200-300 ml/min. In other words, two flow rate regimes can be discerned from the data: one in which the average particle size is strongly flow dependent and another in which the average particle size can be considered as substantially independent of the flow rate. FIG. 12 also shows that average particle sizes appear to be substantially independent of the O:W ratio within the range of 1:5 and 1:10.

These data show that the average particle size can be tuned ("dialed") by changing the flow rates (principally the anti-solvent rate) through the mixer while ensuring that the polydispersity index remains low. In other words, for a given desired average particle size, the flow rates can be selected to achieve the target particle average size.

Example 2

The process described above in Example 1 was again conducted but the polymer concentration in the polymer solution was increased to 2%. Data was collected at both 1:5 and 1:10 O:W ratios.

The results are shown in the table below:

TABLE 2

| O:W ratio | Qo (ml/min) | Qw (ml/min) | Qt (ml/min) | Z-Avg (nm) | PdI | D(v)50 (nm) | D(v)90 (nm) | D(v)10 (nm) |
|---|---|---|---|---|---|---|---|---|
| 1:5 | 73.0 | 365.0 | 438.0 | 110 | 0.058 | 97 | 151 | 68 |
|  | 60.0 | 301.0 | 361.0 | 121 | 0.057 | 109 | 172 | 75 |
|  | 47.0 | 237.0 | 284.0 | 129 | 0.012 | 121 | 177 | 87 |
|  | 34.3 | 172.0 | 206.3 | 137 | 0.059 | 129 | 200 | 88 |
|  | 21.5 | 107.4 | 128.9 | 157 | 0.042 | 155 | 233 | 105 |
|  | 12.9 | 64.4 | 77.3 | 176 | 0.05 | 178 | 264 | 120 |
|  | 4.3 | 21.5 | 25.8 | 207 | 0.061 | 214 | 307 | 150 |
| 1:10 | 46.4 | 463.5 | 509.9 | 119 | 0.058 | 108 | 166 | 75 |
|  | 38.6 | 386.5 | 425.1 | 126 | 0.055 | 115 | 182 | 79 |
|  | 30.1 | 300.0 | 330.1 | 132 | 0.012 | 124 | 183 | 88 |
|  | 21.5 | 214.0 | 235.5 | 140 | 0.059 | 133 | 203 | 93 |
|  | 12.9 | 128.0 | 140.9 | 155 | 0.053 | 152 | 232 | 101 |
|  | 4.3 | 42.9 | 47.2 | 191 | 0.026 | 194 | 283 | 134 |

As in Example 1, PdI was maintained at less than 0.1 for all flow conditions.

The $Z_{ave}$ versus flow rate is plotted in FIG. 12 together with the data in Example 1. The data shows that increasing the polymer concentration from 1% to 2% results in an increase in the average particle size in a controlled fashion and with a similar dependency on the flow rate as that observed for the 1% polymer concentration.

Example 3

The process discussed above in Example 1 was again conducted by utilizing the modified SMX mixer (shown in FIG. 11B) to test the effect of flow rate on average particle size. Using freshly prepared 1 wt % PLGA and 0.5 wt % PVA solutions and maintaining the W:O ratio at 10:1, a series of experiments detailed below were conducted.

a) In the first experiment, the SMX mixer was utilized with a set of pumps with a total flow rate range of 100 to 500 ml min.

b) In the second experiment, the same mixer was used but with another set of pumps with a larger flow rate in a range of 500 to 2000 ml min.

c) In the third experiment, the helical mixer was used with the pumps used in a) but at a single flow rate combination.

d) In the final experiment, the SMX mixer was used with pumps used in b) but at 3 flow rate combinations.

The results are shown in the Table 3 below:

TABLE 3

| Experiment | Qo (ml/min) | Qw (ml/min) | Qt (ml/min) | Z-Ave (nm) | PdI | D10(v) (nm) | D50(v) (nm) | D90(v) (nm) |
|---|---|---|---|---|---|---|---|---|
| a | 10 | 100 | 110 | 232 | 0.115 | 151 | 250 | 425 |
|   | 15 | 150 | 165 | 215 | 0.082 | 147 | 225 | 349 |
|   | 20 | 200 | 220 | 191 | 0.036 | 130 | 194 | 287 |
|   | 25 | 250 | 275 | 185 | 0.068 | 123 | 188 | 290 |
|   | 30 | 300 | 330 | 191 | 0.100 | 111 | 197 | 338 |
|   | 35 | 350 | 385 | 166 | 0.053 | 110 | 166 | 249 |
|   | 45 | 450 | 495 | 149 | 0.074 | 94 | 143 | 227 |
| b | 45 | 450 | 495 | 168 | 0.057 | 112 | 168 | 252 |
|   | 60 | 660 | 660 | 152 | 0.062 | 97 | 148 | 231 |
|   | 75 | 750 | 825 | 140 | 0.064 | 86 | 131 | 212 |
|   | 90 | 900 | 990 | 132 | 0.069 | 81 | 121 | 196 |
|   | 105 | 1050 | 1155 | 127 | 0.076 | 75 | 114 | 190 |
|   | 120 | 1200 | 1320 | 123 | 0.053 | 77 | 112 | 174 |
|   | 135 | 1350 | 1485 | 115 | 0.077 | 67 | 100 | 165 |
|   | 150 | 1500 | 1650 | 121 | 0.074 | 69 | 105 | 179 |
|   | 180 | 1800 | 1980 | 113 | 0.084 | 65 | 97 | 164 |
| C | 45 | 450 | 495 | 121 | 0.151 | 59 | 97 | 199 |
|   | 45 | 450 | 495 | 128 | 0.025 | 84 | 119 | 178 |
| D | 105 | 1050 | 1155 | 128 | 0.049 | 84 | 120 | 181 |
|   | 150 | 1500 | 1650 | 111 | 0.078 | 68 | 98 | 156 |
|   | 180 | 1800 | 1980 | 107 | 0.062 | 63 | 91 | 147 |

Figure 13:
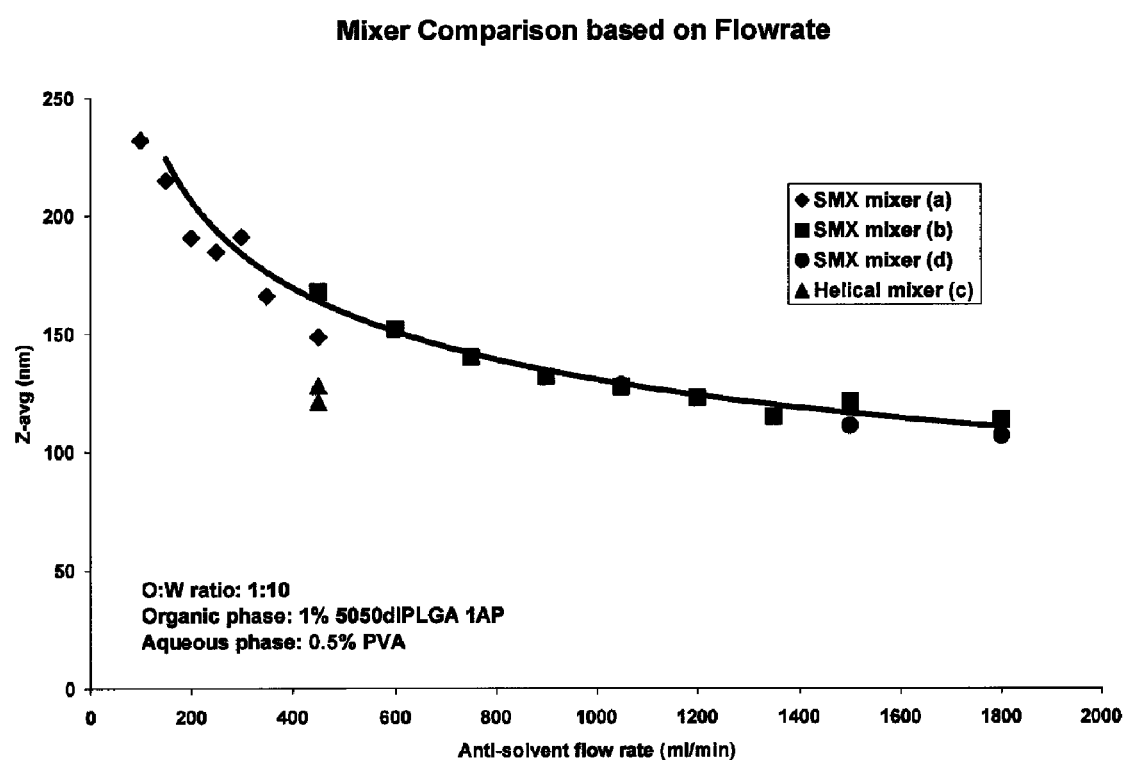
FIG. 13 presents data corresponding to $Z_{ave}$ as a function of anti-solvent flow rate for nanoparticles generated in two prototype devices according to the teachings of the invention.

The data shows that in most cases the PdI was maintained at less than 0.1. A plot of Z, versus anti-solvent flow rate is shown in FIG. 13. From this Figure, it can be seen that the data from the three experiments using the SMX mixer are comparable and may be represented by a single curve. The data obtained by utilizing the helical mixer indicates that smaller sized particles were generated compared to the particles generated by utilizing the SMX mixer for the same flow rate. This can be due to a greater mixing intensity achieved in the helical mixer device, which has a smaller diameter.

Example 4

Utilizing the helical mixer shown in FIG. 11A, the following process was employed to fabricate a 3-gram batch of docetaxel PEGylated nanoparticles.

2.52 grams of docetaxel custom conjugated PLGA (Mw=6.6 kD, Mn=3.0 kD, drug loading: 8%, AMRI Albany, N.Y.), and 0.480 grams of 5050☐L-PLGA mPEG 2 kD (Mw: 10.6 kD, mPEG Mw: 2.0 kD, Lakeshore Biomaterials, Birmingham, Ala.) were dissolved in 237 grams of acetone at room temperature. Separately, a total of 15 grams of poly vinyl alcohol (PVA) (80% hydrolyzed, Mw 9-10 kD, Aldrich, St. Louis, Mo.) was dissolved in 3 kilograms of water at room temperature. Each solution was translucent and visually free of undissolved material.

Referring to FIG. 7, the flow of the aqueous phase (antisolvent) was initiated at a flow rate of 220 ml/min via the aqueous inlet through the conduit of the device in which the static mixer was disposed. Once the flow of the aqueous phase was established, the flow of the polymer solution was initiated at 22 ml/min from an organic solution vessel (not shown) through the organic inlet into the flowing stream of the aqueous phase. Once the organic solution vessel had emptied, the organic pump was turned off and the aqueous pump remained on for several moments to flush out the mixer. The recovered suspension collected in a collection vessel was milky white and no large particles were distinguishable by the naked eye.

The nanoparticle suspension was diafiltered and concentrated in the following two-step process. The suspension was initially diafiltered to remove dissolved PVA and acetone by recirculation through a 300 kD MWCO filter cassette (Pall Omega Centramate Medium Screen cassette, 0.093 m²), at a recirculation flow rate of 200 ml/min and a transmembrane pressure (TMP) of 1.5 bar using 44 L of deionized water. Upon completion, the nanoparticles suspension was drained from the cassette and the cassette was rinsed twice by recirculating fresh deionized water through the cassette and respective tubing (2×250 ml). The rinse volumes were collected and combined with the initially recovered nanoparticles suspension.

The washed nanoparticles suspension was subsequently concentrated using three smaller 300 kD MWCO filters (Millipore Pellicon XL, 50 cm² with Biomax membrane) plumbed in parallel at a recirculation rate of about 25 ml/min and a TMP of 1 bar. Drug concentration was continuously monitored by HPLC assay as the suspension volume was reduced. A portion of the suspension was collected when the drug content level reached 1.7 mg/ml and the remainder was collected at a drug content level of 3.2 mg/ml. Each suspension was stored at 4° C. The yield based on docetaxel recovery was about 85.5%.

Figure 14:
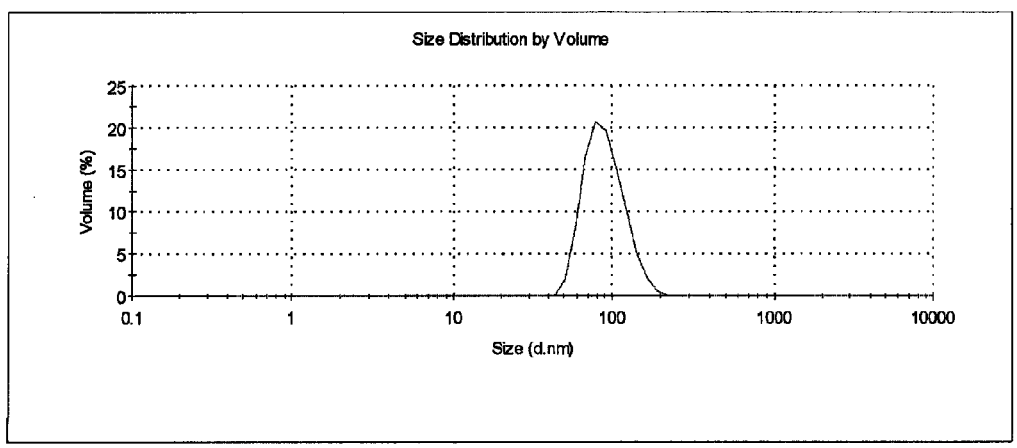
FIG. 14 shows particle size distribution exhibited by polymeric nanoparticles generated by employing a prototype device according to the teachings of the invention.

FIG. 14 shows the particle size distribution obtained by the Zetasizer. The average particle size ($Z_{ave}$) was measured to be about 97.5 nm, Dv90 (defined as the particle size below which the sizes of 90% of the particles lies) was determined to be about 130.3 nm, and Dv50 (defined as the particle size below which the sizes of 50% of the particle lie) was determined to be about 85.2 nm. Further, the polydispersity index (PdI) was measured to be about 0.066.

Example 5

Utilizing the modified SMX mixer shown in FIG. 11B, the following process was employed to fabricate a 10-gram batch of docetaxel PEGylated nanoparticles. 6.044 grams of docetaxel custom conjugated PLGA (Mw=9.8 kD, Mn=5.7 kD, drug loading: 7.6%, AMRI Albany, N.Y.), and 4.003 grams of 5050☐L-PLGA mPEG 2 kD (Mw: 13.0 kD, mPEG Mw: 2.0 kD, Lakeshore Biomaterials, Birmingham, Ala.) were dissolved in 791 grams of acetone at room temperature. Separately, 11 L of 0.5% solution of PVA was prepared by combining 1.1 L of previously prepared stock solution of 5% PVA with 9.9 L of RODI water. (The stock solution was prepared by dissolving 110 gm of PVA (80% hydrolyzed, Mw: 9-10 kD, Sigma-Aldrich, St. Louis, Mo.) into 2200 ml of RODI water and heating the solution at 80° C. for 3 hr. The solution was cooled to room temperature, filtered and stored at 4° C.

Referring to FIG. 7, the flow of the aqueous phase (antisolvent) was initiated at a flow rate of 608 ml/min via the aqueous inlet through the conduit of the device in which the static mixer was disposed. Once the flow of the aqueous phase was established, the flow of the polymer solution was initiated at 60.8 ml/min from an organic solution vessel (not shown) through the organic inlet into the flowing stream of the aqueous phase. Once the organic solution vessel was empty, the organic pump was turned off and the aqueous pump remained on for several moments to flush out the mixer. The recovered suspension, approximately 11 liters, was collected in 20 liter polypropylene carboy.

The nanoparticle suspension was diafiltered and concentrated using a tangential flow filter (TFF) (GE Healthcare hollow fiber cartridge, polysulfone membrane, 500 kD NMWC, 0.14 m²) in a three-step process. Using a recirculation rate of 1160 ml/min and a transmembrane pressure (TMP) of less than 20 psi, the suspension was initially concentrated to approximately 1 liter, diafiltered with 12 liters of RODI water, and concentrated a final time to 206 ml. The suspension was recovered and measured by HPLC for docetaxel content and stored at 4° C. The yield based on docetaxel recovery was about 96%.

Figure 15:
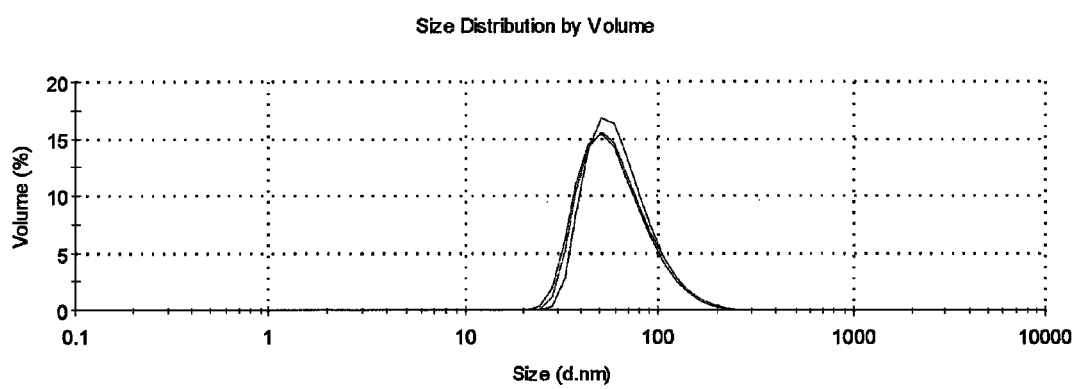
FIG. 15 shows three graphs corresponding to three measurements of the particle size distribution exhibited by a plurality of polymeric nanoparticles generated by employing a prototype device according to the teachings of the invention as discussed below in Example 5.

FIG. 15 shows three graphs corresponding to three measurements, obtained by Malvern Zetasizer Model Nano S (Malvern Instruments, Southborough, Mass.), of the particle size distribution of the nanoparticles. The average particle size ($Z_{ave}$) was measured to be about 80.35 nm, Dv90 (defined as the particle size below which the sizes of 90% of the particles lies) was determined to be about 103 nm, and Dv50 (defined as the particle size below which the sizes of 50% of the particle lie) was determined to be about 69.2 nm. Further, the polydispersity index (PdI) was measured to be 0.052.

All publications referred to herein, including patents, published patent applications, articles, among others, are hereby incorporated by reference in their entirety.

Those having ordinary skill in the art will appreciate that various changes can be made to the above embodiments without departing from the scope of the invention.

What is claimed is:

1. A process for forming polymeric nanoparticles, comprising:
   generating a mixed flowing stream of an anti-solvent, and
   introducing a polymer-carrying liquid into said mixed flowing stream of the anti-solvent so as to form polymeric nanoparticles.

2. The process of claim 1, further comprising separating the polymeric nanoparticles from the anti-solvent stream.

3. The process of claim 1, further comprising controlling a flow rate of said mixed flowing stream of the anti-solvent so as to adjust an average particle size of said polymeric nanoparticles.

4. The process of claim 1, further comprising selecting a flow rate of said mixed flowing stream of the anti-solvent such that said polymeric nanoparticles exhibit an average particle size equal to or less than about 200 nm.

5. The process of claim 1, further comprising selecting a flow rate of said mixed flowing stream of the anti-solvent such that said polymeric nanoparticles exhibit an average particle size equal to or less than about 100 nm.

6. The process of claim 5, wherein said polymeric nanoparticles exhibit an average particle size in a range of about 40 nm to about 100 nm.

7. The process of claim 1, wherein said polymeric nanoparticles exhibit a polydispersity index less than about 0.25.

8. The process of claim 1, wherein said polymeric nanoparticles exhibit a polydispersity index in a range of about 0.05 to about 0.1.

9. The process of claim 1, wherein said polymer-carrying liquid is introduced as a liquid stream into said mixed flowing stream of the anti-solvent.

10. The process of claim 9, wherein a ratio of a flow rate of said mixed flowing stream of the anti-solvent relative to a flow rate of said polymer-carrying liquid stream is in a range of about 1:1 to about 100:1.

11. The process of claim 9, wherein a ratio of a flow rate of said mixed flowing stream of the anti-solvent relative to a flow rate of said polymer-carrying liquid stream is at least about 5:1.

12. The process of claim 9, wherein a ratio of a flow rate of said mixed flowing stream of the anti-solvent relative to a flow rate of said polymer-carrying liquid stream is at least about 10:1.

13. The process of claim 1, wherein said anti-solvent flowing stream exhibits an average axial flow velocity in a range of about 1 cm/sec to about 100 cm/sec.

14. The process of claim 1, wherein said mixed flowing stream of the anti-solvent presents a substantially isotropic mixed anti-solvent environment to the incoming polymer-carrying liquid.

15. The process of claim 14, wherein said mixed anti-solvent environment is substantially isotropic over at least about 50% of the volume of said conduit.

16. The process of claim 1, wherein said polymer-carrying liquid comprises a polymer dissolved in a process solvent, wherein said process solvent is partially miscible with said anti-solvent.

17. The process of claim 16, wherein said polymer is any of poly(lactide-co-glycolide), poly(lactide), poly(epsilon-caprolactone), poly(isobutylcyanoacrylate), poly(isohexylcyanoacrylate), poly(n-butylcyanoacrylate), poly(acrylate), poly(methacrylate), poly(lactide)-poly(ethylene glycol), poly(lactide-co-glycolide)-poly (ethylene glycol), poly(epsilon-caprolactone)-poly(ethylene glycol), and poly(hexadecylcyanoacrylate-co-poly(ethylene glycol) cyanoacrylate).

18. The process of claim 1, wherein said polymer-carrying liquid comprises at least one additive.

19. The process of claim 18, wherein said one additive comprises any of a therapeutic agent or an imaging agent.

20. The process of claim 19, wherein said therapeutic or imaging agent is embedded in said polymer.

21. The process of claim 19, wherein said therapeutic or imaging agent is conjugated to said polymer.

22. The process of claim 19, wherein said therapeutic agent is any of an anti-neoplastic agent, an anti-inflammatory agent, or a cardiovascular active agent.

23. The process of claim 19, wherein said therapeutic agent is any of a taxane, an epothilone, a boronic acid proteasome inhibitor, and an anti-biotic.

24. The process of claim 19, wherein said therapeutic agent is an anti-metabolite.

25. The process of claim 16, wherein said process solvent comprises any of acetone, ether, alcohol, tetrahydrofuran, 2-pyrrolidone, N-Methyl-2-pyrrolidone (NMP), dimethylformamide (DMF), dimethylacetamide (DMA), methyl acetate, ethyl formate, methyl ethyl ketone (MEK), methyl isobutyl ketone (MIBK), methyl propyl ketone, isopropyl ketone, isopropyl acetate, acetonitrile (MeCN) and dimethyl sulfoxide (DMSO).

26. The process of claim 1, wherein said anti-solvent comprises an aqueous solution.

27. The process of claim 26, wherein said aqueous solution comprises any of an alcohol, an ether, and water.

28. The process of claim 1, wherein said anti-solvent comprises any of an organic solvent or a mixture of two or more organic solvents.

29. The process of claim 1, wherein said anti-solvent comprises any of methanol, ethanol, n-propanol, isopropanol, n-butanol, and ethyl ether.

30. The process of claim 1, wherein said anti-solvent comprises a colloid stabilizer.

31. The process of claim 30, wherein said colloid stabilizer comprises any of poly(vinyl alcohol), Dextran and pluronic F68, poly (vinyl pyrrolidone), solutol, Tween 80, poloxamer, carbopol, poly-ethylene glycol, sodium dodecyl sulfate, poly (ϵ-caprolactone), peptides, and carbohydrates.

32. The process of claim 1, wherein said polymer-carrying liquid comprises a polymer solution.

33. The process of claim 1, wherein said polymer-carrying liquid comprises a polymer dispersion.

34. The process of claim 1, wherein said polymer-carrying liquid comprises a mixed polymer solution/dispersion.

35. A population of polymeric nanoparticles, comprising:
a plurality of polymeric nanoparticles having poly(lactic-co-glycolic acid) (PLGA) as at least one polymeric component,
wherein said polymeric nanoparticles exhibit an average particle size equal to or less than about 200 nm and a polydispersity index less than about 0.25.

36. The population of polymeric nanoparticles of claim 35, wherein said polymeric nanoparticles exhibit a polydispersity index in a range of about 0.05 to about 0.1.

37. The population of polymeric nanoparticles of claim 35, wherein said polymeric nanoparticles exhibit an average particle size in a range of about 40 nm to about 100 nm.

38. The population of polymeric nanoparticles of claim 35, wherein said polymeric nanoparticles comprise any of a therapeutic agent or an imaging agent.

39. The population of polymeric nanoparticles of claim 38, wherein said therapeutic agent is any of a taxane, an epothilone, a boronic acid proteasome inhibitor, and an antibiotic.

40. The population of polymeric nanoparticles of claim 38, wherein said therapeutic agent is an anti-neoplastic agent.

41. The population of polymeric nanoparticles of claim 40, wherein said anti-neoplastic agent is a taxane.

42. The population of polymeric nanoparticles of claim 41, wherein said taxane is any of paclitaxel, docetaxel, larotaxel and cabazitaxel.

43. The population of polymeric nanoparticles of claim 35, wherein said population includes at least about 10 grams of said nanoparticles.

44. The population of polymeric nanoparticles of claim 35, wherein said population includes at least about 50 grams of said nanoparticles.

45. The population of polymeric nanoparticles of claim 35, wherein said population includes at least about 100 grams of said nanoparticles.

46. The population of polymeric nanoparticles of claim 35, wherein said population includes at least about 500 grams of said nanoparticles.

47. The population of polymeric nanoparticles of claim 35, wherein said population comprises a lyoprotectant.

48. A process for forming polymeric nanoparticles, which comprises:
a) creating a mixed flowing stream of an anti-solvent;
b) introducing a polymer-carrying liquid into the mixed flowing stream of the anti-solvent so as to form polymeric nanoparticles;
c) evaluating a sample of said polymeric nanoparticles to determine if the polymeric nanoparticles meet a pre-defined criterion,
thereby forming said nanoparticles.

49. The process of claim 48, wherein said criterion is any of an average particle size, polydispersity, or drug loading.

50. The process of claim 48, wherein if said sample of nanoparticles fails to meet said criterion, a parameter is adjusted, and steps a) and b) are carried out under the adjusted parameter.

51. The process of claim 50, wherein said parameter is any of: a flow rate of the anti-solvent and/or the polymer-carrying liquid, a concentration of a polymer in the polymer-carrying liquid, an average axial flow velocity of the mixed flowing stream of the anti-solvent and/or that of the polymer-carrying liquid.

52. A process for forming polymeric nanoparticles, which comprises:
a) creating a mixed flowing stream of an anti-solvent;
b) introducing a polymer-carrying liquid into the mixed flowing stream of the anti-solvent so as to form polymeric nanoparticles;
c) evaluating a sample of said polymeric nanoparticles to determine if at least one attribute of the polymeric nanoparticles meets a reference value,
thereby forming said nanoparticles.

53. The process of claim 52, wherein said attribute is any of an average particle size, polydispersity index, or drug loading.

54. The process of claim 52, wherein said attribute is any of a release parameter or a manufacturing specification.

55. The process of claim 52, wherein the reference value is set by a regulatory agency, a compendial authority, or a manufacturer of nanoparticles.

56. The process of claim 55, wherein said regulatory agency is the FDA.

57. The process of claim 52, wherein, responsive to whether the attribute meets said reference value for that attribute, a further decision or step is taken.

58. The process of claim 57, wherein said further decision or step comprises one in which the sample is classified, selected, rejected, accepted or discarded, released or withheld, processed into a drug product, shipped, moved to a different location, formulated, labeled, packaged, released into commerce, exported, imported, or sold or offered for sale.

59. The process of claim 14, wherein said mixed anti-solvent environment is substantially isotropic over at least about 60% of the volume of said conduit.

60. The process of claim 14, wherein said mixed anti-solvent environment is substantially isotropic over at least about 70% of the volume of said conduit.

61. The process of claim 14, wherein said mixed anti-solvent environment is substantially isotropic over at least about 90% of the volume of said conduit.

62. The process of claim 14, wherein said mixed anti-solvent environment is substantially isotropic over 100% of the volume of said conduit.

* * * * *